US008247535B2

(12) United States Patent
Heinrichs et al.

(10) Patent No.: US 8,247,535 B2
(45) Date of Patent: Aug. 21, 2012

(54) DIRECTED EVOLUTION OF GRG31 EPSP SYNTHASE ENZYME

(75) Inventors: Volker Heinrichs, Raleigh, NC (US); Laura Cooper Schouten, Pittsboro, NC (US); Brian Vande Berg, Durham, NC (US)

(73) Assignee: Athenix Corp., Research Triangle Park, NC (US)

(*) Notice: Subject to any disclaimer, the term of this patent is extended or adjusted under 35 U.S.C. 154(b) by 0 days.

(21) Appl. No.: 13/101,351

(22) Filed: May 5, 2011

(65) Prior Publication Data

US 2011/0223648 A1 Sep. 15, 2011

Related U.S. Application Data

(62) Division of application No. 12/362,774, filed on Jan. 30, 2009, now Pat. No. 7,960,616.

(60) Provisional application No. 61/025,406, filed on Feb. 1, 2008.

(51) Int. Cl.
*C12N 15/88* (2006.01)
*A61K 38/43* (2006.01)
*A61K 380/00* (2006.01)

(52) U.S. Cl. ............... 530/350; 435/462; 435/440

(58) Field of Classification Search .................. None
See application file for complete search history.

(56) References Cited

U.S. PATENT DOCUMENTS

| | | | |
|---|---|---|---|
| 5,094,945 A | 3/1992 | Comai | |
| 5,188,642 A | 2/1993 | Shah et al. | |
| 5,312,910 A | 5/1994 | Kishore et al. | |
| 6,040,497 A | 3/2000 | Spencer et al. | |
| 6,225,114 B1 | 5/2001 | Eichholtz et al. | |
| RE37,287 E | 7/2001 | Lebrun et al. | |
| 6,566,587 B1 | 5/2003 | Lebrun et al. | |
| 6,867,293 B2 | 3/2005 | Andrews et al. | |
| 7,045,684 B1 | 5/2006 | Held et al. | |
| 7,141,722 B2 | 11/2006 | Fincher et al. | |
| 7,183,110 B2 | 2/2007 | Barry et al. | |
| 7,214,535 B2 | 5/2007 | Sun et al. | |
| 2003/0049814 A1 | 3/2003 | Andrews et al. | |
| 2003/0079246 A1 | 4/2003 | Andrews et al. | |
| 2003/0200560 A1 | 10/2003 | Warner et al. | |
| 2003/0233675 A1 | 12/2003 | Cao et al. | |
| 2004/0148650 A1 | 7/2004 | Baerson et al. | |
| 2005/0223436 A1 | 10/2005 | Lin et al. | |
| 2006/0143727 A1 | 6/2006 | Alibhai et al. | |
| 2006/0150270 A1 | 7/2006 | Hammer et al. | |
| 2006/0253921 A1 | 11/2006 | Carozzi et al. | |
| 2007/0136840 A1 | 6/2007 | Peters et al. | |
| 2007/0289035 A1 | 12/2007 | Vande Berg et al. | |
| 2007/0294785 A1 | 12/2007 | Volker | |
| 2007/0300326 A1 | 12/2007 | Peter et al. | |

FOREIGN PATENT DOCUMENTS

| | | |
|---|---|---|
| EP | 1103616 | 5/2001 |
| EP | 1510581 | 3/2005 |
| WO | 2004056179 | 7/2004 |
| WO | 2006110586 | 10/2006 |
| WO | 2007082269 | 7/2007 |
| WO | 2007146765 | 12/2007 |
| WO | 2007146980 | 12/2007 |

OTHER PUBLICATIONS

Eschenburg, Susanne ei al., "How the mutation glycirie96 to alanine confers glyphosate insensitivity to 5-enolpyruvyl shikimate-3-phosphate synthase from *Escherichia coli*", Planta (Berlin), Nov. 2002, pp. 129-135, vol. 216, No. 1.
Geneseq Database Report for Accession No. ADS21268, first entry, Dec. 2. 2004.
Geneseq Database Report for Accession No. ADT42596, first entry, Dec. 2, 2004.
NCBI Database Report for Accession No. BAB06432, Direct Submission on Mar. 22, 2000.
NCBI Database Report for Accession No. NP_824218, Direct Submission on Apr. 8, 2002.
NCBI Database Report for Accession No. NP_629359, Direct Submission on May 28, 2002.
NCBI Database Report for Accession No. BAD59440, Direct Submission on Sep. 26, 2003.
NCBI Database Report for Accession No. BAD63759, Direct Submission on Oct. 19, 2003.
NCBI Database Report for Accession No. YP_075248, Direct Submission on Sep. 7, 2004.
NCBI Database Report for Accession No. YP_098022, Direct Submission on Oct. 1, 2004.
NCBI Database Report for Accession No. ZP_00413033, Direct Submission on Jun. 1, 2005.
NCBI Database Report for Accession No. ZP_832132, Direct Submission Oct. 25, 2006.
Pipke, R. et al., "Isolation and Characterization of a Mutant of *Athrobacter* sp. Strain GLP—1 Which Utilizes the Herbicide Glyphosate as Its Sole Source of Phosphorus and Nitrogen", Applied and Environmental Microbiology, Nov. 1998, pp. 2868-2870, vol. 54, No. 11.

(Continued)

*Primary Examiner* — Anand Desai
*Assistant Examiner* — Samuel Liu

(57) ABSTRACT

Compositions and methods for conferring herbicide resistance or tolerance to bacteria, plants, plant cells, tissues and seeds are provided. Compositions include polynucleotides encoding herbicide resistance or tolerance polypeptides, vectors comprising those polynucleotides, and host cells comprising the vectors. The nucleotide sequences of the invention can be used in DNA constructs or expression cassettes for transformation and expression in organisms, including microorganisms and plants. Compositions also include transformed bacteria, plants, plant cells, tissues, and seeds. In particular, isolated polynucleotides encoding glyphosate resistance or tolerance polypeptides are provided, particularly polypeptide variants of SEQ ID NO:2 and 4. Additionally, amino acid sequences corresponding to the polynucleotides are encompassed. In particular, the present invention provides for isolated polynucleotides containing nucleotide sequences encoding the amino acid sequence shown in SEQ ID NO:7-28, or the nucleotide sequence set forth in SEQ ID NO:29 or 30.

3 Claims, No Drawings

OTHER PUBLICATIONS

Sun, Yi-Cheng et al., "Novel AroA with Hight Tolerance to Glyphosate, Encoded by a Gene of *Pseudomonas putida* 4G-1 Isolated from an Extremely Polluted Environment in China", Applied and Environmental Microbiology, Aug. 2005, pp. 4771-4776, vol. 71, No. 8.

Takami et al., "Complete genome sequence of the alkaliphilic bacterium *Bacillus halodurans* and genomic sequence comparison with *Bacillus subtilis*", Nucleic Acids Research, 2000, pp. 4317-4331, vol. 28, No. 21.

Uniprot Database Report for accession No. Q9K9D5, Direct Submission Oct. 1, 2000.

Healy-Fried, M.L. et al., "Structural Basis of Glyphosate Tolerance Resulting from Mutations of Pro 101 in *Escherichia coli* 5-Enolpyruvylshikimate-3-phosphate Synthase", J. Biol. Chem., Nov. 2007, pp. 32949-32955, vol. 282, No. 45.

Kahrizi, D. et al., "Simultaneous Substitution of Gly96 to Ala and Alal83 to Thr in 5-enolpyruvylshikimate-3-phosphate Synthase Gene of *E-coli* (k12) and Transformation of Rapeseed (*Brassica napus* L.) in order to Make Tolerance to Glyphosate", Plant Cell Rep., Jan. 2007, pp. 95-104. vol. 26, No. 1.

DIRECTED EVOLUTION OF GRG31 EPSP SYNTHASE ENZYME

CROSS-REFERENCE TO RELATED APPLICATIONS

This application is a divisional of U.S. application Ser. No. 12/362,774, filed Jan. 30, 2009, which claims the benefit of U.S. Provisional Application No. 61/025,406, filed Feb. 1, 2008, which is hereby incorporated in its entirety by reference herein.

REFERENCE TO SEQUENCE LISTING SUBMITTED ELECTRONICALLY

The official copy of the sequence listing is submitted electronically via EFS-Web as an ASCII formatted sequence listing with a file named "APA055US01DSEQLIST.txt", created on Apr. 26, 2011, and having a size of 104 kilobytes and is filed concurrently with the specification. The sequence listing contained in this ASCII formatted document is part of the specification and is herein incorporated by reference in its entirety.

FIELD OF THE INVENTION

This invention relates to plant molecular biology, particularly novel EPSP synthase polypeptides that confer improved resistance or tolerance to the herbicide glyphosate.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid (S3P) to 5-enolpyruvyl-3-phosphoshikimic acid. Inhibition of this enzyme (5-enolpyruvylshikimate-3-phosphate synthase; referred to herein as "EPSP synthase", or "EPSPS") kills plant cells by shutting down the shikimate pathway, thereby inhibiting aromatic amino acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945).

U.S. Pat. No. 6,040,497 reports mutant maize EPSP synthase enzymes having substitutions of threonine to isoleucine at position 102 and proline to serine at position 106 (the "TIPS" mutation). Such alterations confer glyphosate resistance upon the maize enzyme. A mutated EPSP synthase from *Salmonella typhimurium* strain CT7 confers glyphosate resistance in bacterial cells, and is reported to confer glyphosate resistance upon plant cells (U.S. Pat. Nos. 4,535,060; 4,769, 061; and 5,094,945). He et al. ((2001) *Biochim et Biophysica Acta* 1568:1-6) have developed EPSP synthases with increased glyphosate tolerance by mutagenesis and recombination between the *E. coli* and *Salmonella typhimurium* EPSP synthase genes, and suggest that mutations at position 42 (T42M) and position 230 (Q230K) are likely responsible for the observed resistance. Subsequent work (He et al. (2003) *Biosci. Biotech. Biochem.* 67:1405-1409) shows that the T42M mutation (threonine to methionine) is sufficient to improve tolerance of both the *E. coli* and *Salmonella typhimurium* enzymes. Due to the many advantages herbicide resistance plants provide, herbicide resistance genes improved glyphosate resistance activity are desirable.

An alternate method for mutagenesis is the "permutational mutagenesis" method described in U.S. Patent Application No. 60/813,095, filed Jun. 13, 2006.

SUMMARY OF INVENTION

Compositions and methods for conferring resistance or tolerance to are provided. Compositions include EPSP synthase enzymes that are resistant to glyphosate herbicide, and nucleic acid molecules encoding such enzymes, vectors comprising those nucleic acid molecules, and host cells comprising the vectors. The compositions include nucleic acid molecules encoding herbicide resistance polypeptides, including those encoding polypeptide variants of SEQ ID NO:2 and 4. In various embodiments, the polypeptide variants are set forth in SEQ ID NOs:7-28. The coding sequences can be used in DNA constructs or expression cassettes for transformation and expression in organisms, including microorganisms and plants. Compositions also comprise transformed bacteria, plants, plant cells, tissues, and seeds that are glyphosate resistant by the introduction of the compositions of the invention into the genome of the organism. Where the organism is a plant, the introduction of the sequence allows for glyphosate containing herbicides to be applied to plants to selectively kill glyphosate sensitive weeds or other untransformed plants, but not the transformed organism. The sequences can additionally be used a marker for selection of plant cells growing under glyphosate conditions.

Methods for identifying an EPSP synthase enzyme with glyphosate resistance activity are additionally provided. The methods comprise identifying additional EPSP synthase sequences that are resistant to glyphosate based on the presence of the domain of the invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is drawn to compositions and methods for regulating herbicide resistance in organisms, particularly in plants or plant cells. The methods involve transforming organisms with nucleotide sequences encoding the glyphosate resistance gene of the invention. The nucleotide sequences of the invention are useful for preparing plants that show increased tolerance to the herbicide glyphosate. Thus, by "glyphosate resistance" or "glyphosate tolerance" gene of the invention is intended the nucleotide sequence encoding the amino acid sequence set forth in any one of SEQ ID NO:7-28, and fragments and variants thereof that encode a glyphosate resistance or tolerance polypeptide. Likewise, a "glyphosate resistance" or "glyphosate tolerance" polypeptide of the invention is a polypeptide having the amino acid sequence set forth in SEQ ID NO:7-28, and fragments and variants thereof, that confer glyphosate resistance or tolerance to a host cell.

A. Isolated Polynucleotides, and Variants and Fragments Thereof

In some embodiments, the present invention comprises isolated, recombinant, or purified polynucleotides. An "isolated" or "purified" polynucleotide or polypeptide, or biologically active portion thereof, is substantially free of other cellular material, or culture medium when produced by recombinant techniques, or substantially free of chemical precursors or other chemicals when chemically synthesized. By "biologically active" is intended to possess the desired biological activity of the native polypeptide, that is, retain herbicide resistance activity. An "isolated" polynucleotide may be free of sequences (for example, protein encoding sequences) that naturally flank the nucleic acid (i.e., sequences located at the 5' and 3' ends of the nucleic acid) in the genomic DNA of the organism from which the polynucleotide is derived. For purposes of the invention, "isolated" when used to refer to polynucleotides excludes isolated chromosomes. For example, in various embodiments, the isolated glyphosate resistance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived.

Polynucleotides of the invention include those that encode glyphosate-resistant polypeptides that are variants of SEQ ID NO:2 and 4. In particular, the polynucleotides encode a variant of SEQ ID NO:2 having one or more substitutions at the positions corresponding to amino acid residues 75, 77, 77, 78, 81, 82, 86, 87, 88, and 95 of SEQ ID NO:2, or substitutions at one or more positions corresponding to amino acid positions 90, 145, 350, or 410 of SEQ ID NO:4. In some embodiments, the variants comprise one or more of the following: a cysteine residue at the position corresponding to amino acid position 75 of SEQ ID NO:2; an aspartic acid residue at the position corresponding to amino acid position 76 of SEQ ID NO:2; an asparagine, alanine, glutamine, or threonine residue at the position corresponding to amino acid position 77 of SEQ ID NO:2; a serine residue at the position corresponding to amino acid position 78 of SEQ ID NO:2; a serine or glycine residue at the position corresponding to amino acid position 81 of SEQ ID NO:2; a valine, threonine, leucine, or phenylalanine residue at the position corresponding to amino acid position 82 of SEQ ID NO:2; an alanine residue at the position corresponding to amino acid position 86 of SEQ ID NO:2; a glycine residue at the position corresponding to amino acid position 87 of SEQ ID NO:2; a phenylalanine, valine, leucine, or histidine residue at the position corresponding to amino acid position 88 of SEQ ID NO:2; a serine, glutamine, or threonine residue at the position corresponding to amino acid position 95 of SEQ ID NO:2; a valine, serine, arginine, glutamine, glutamic acid, or threonine residue at the position corresponding to amino acid position 206 of SEQ ID NO:2; a lysine, glutamine, arginine, serine, or threonine residue at the position corresponding to amino acid position 215 of SEQ ID NO:2; an isoleucine residue at the position corresponding to amino acid position 90 of SEQ ID NO:4; a glutamine residue at the position corresponding to amino acid position 145 of SEQ ID NO:4; a threonine residue at the position corresponding to amino acid position 350 of SEQ ID NO:4; and a methionine residue at the position corresponding to amino acid position 410 of SEQ ID NO:4. In various embodiments, the variants are selected from any one of SEQ ID NO:7-28, as well as the synthetic nucleotide sequences set forth in SEQ ID NO:29 or 30.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

The present invention further contemplates variants and fragments of the polynucleotides described herein. A "fragment" of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 contiguous nucleotides, or up to the number of nucleotides present in a full-length polynucleotide disclosed herein depending upon the intended use (e.g., an EPSP synthase polynucleotide comprising SEQ ID NO:1). By "contiguous" nucleotides is intended nucleotide residues that are immediately adjacent to one another.

Fragments of the polynucleotides of the present invention generally will encode polypeptide fragments that retain the biological activity of the full-length glyphosate resistance protein; i.e., herbicide-resistance activity. By "retains herbicide resistance activity" is intended that the fragment will have at least about 30%, at least about 50%, at least about 70%, at least about 80%, 85%, 90%, 95%, 100%, 110%, 125%, 150%, 175%, 200%, 250%, at least about 300% or greater of the herbicide resistance activity of the full-length glyphosate resistance protein disclosed herein as SEQ ID NO:2 or 4. Methods for measuring herbicide resistance activity are well known in the art. See, for example, U.S. Pat. Nos. 4,535,060, and 5,188,642, each of which are herein incorporated by reference in their entirety.

A fragment of a polynucleotide that encodes a biologically active portion of a polypeptide of the invention will encode at least about 15, 25, 30, 50, 75, 100, 125, 150, 175, 200, 250, 300, 350, 400 contiguous amino acids, or up to the total number of amino acids present in a full-length polypeptide of the invention.

The invention also encompasses variant polynucleotides as described supra. "Variants" of the polynucleotide also include those sequences that encode the polypeptides disclosed herein but that differ conservatively because of the degeneracy of the genetic code, as well as those that are sufficiently identical.

The term "sufficiently identical" is intended a polypeptide or polynucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art will recognize that these values can be appropriately adjusted to determine corresponding identity of polypeptides encoded by two polynucleotides by taking into account codon degeneracy, amino acid similarity, reading frame positioning, and the like.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide resistance. These herbicide resistance proteins are encompassed in the present invention and may be used in the methods of the present invention.

Naturally occurring allelic variants can be identified with the use of well-known molecular biology techniques, such as polymerase chain reaction (PCR) and hybridization techniques as outlined below. Variant polynucleotides also include synthetically derived polynucleotides that have been generated, for example, by using site-directed or other mutagenesis strategies but which still encode the polypeptide having the desired biological activity.

The skilled artisan will further appreciate that changes can be introduced by further mutation of the polynucleotides of the invention thereby leading to further changes in the amino acid sequence of the encoded polypeptides, without altering the biological activity of the polypeptides. Thus, variant isolated polynucleotides can be created by introducing one or more additional nucleotide substitutions, additions, or deletions into the corresponding polynucleotide encoding the EPSP synthase domain disclosed herein, such that one or more amino acid substitutions, additions or deletions are introduced into the encoded polypeptide. Further mutations can be introduced by standard techniques, such as site-directed mutagenesis and PCR-mediated mutagenesis, or gene shuffling techniques. Such variant polynucleotides are also encompassed by the present invention.

Variant polynucleotides can be made by introducing mutations randomly along all or part of the coding sequence, such as by saturation mutagenesis, and the resultant mutants can be screened for the ability to confer herbicide resistance activity to identify mutants that retain activity.

Gene shuffling or sexual PCR procedures (for example, Smith (1994) *Nature* 370:324-325; U.S. Pat. Nos. 5,837,458; 5,830,721; 5,811,238; and 5,733,731, each of which is herein incorporated by reference) can be used to further modify or enhance polynucleotides and polypeptides disclosed herein (for example, polypeptides that confer glyphosate resistance). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in different clones becoming mixed and accumulating in some of the resulting sequences. Multiple cycles of selection and shuffling have led to the functional enhancement of several enzymes (Stemmer (1994) *Nature* 370:389-391; Stemmer (1994) *Proc. Natl. Acad. Sci. USA* 91:10747-10751; Crameri et al. (1996) *Nat. Biotechnol.* 14:315-319; Zhang et al. (1997) *Proc. Natl. Acad. Sci. USA* 94:4504-4509; and Crameri et al. (1997) *Nat. Biotechnol.* 15:436-438). Such procedures could be performed, for example, on polynucleotides encoding polypeptides disclosed herein.

Additional methods for generating variants include subjecting a cell expressing a protein disclosed herein (or library thereof) to a specific condition that creates a stress to the activity of the protein. Specific conditions can include (but are not limited to) changes in temperature, changes in pH, and changes in the concentrations of substrates or inhibitors. The protein library can be subjected to these conditions during the time of protein expression (e.g., in *E. coli* or other host) or following creation of a protein extract, or following protein purification.

The functional or enzymatic activity of the protein library that has been subjected to a stress condition can then be compared to the wild-type protein to identify proteins with improved properties. This activity comparison can be carried out as part of a growth screen or alternatively as part of an enzymatic assay that quantifies the activity of the protein. The properties that can be identified as improved can include glyphosate tolerance, changes in kinetic constants (including $K_m$, $K_i$, $V_{max}$), protein stability, protein thermostability, or protein temperature optimum.

B. Isolated Proteins and Variants and Fragments Thereof

Herbicide resistance polypeptides are also encompassed within the present invention. An herbicide resistance polypeptide that is substantially free of cellular material includes preparations of polypeptides having less than about 30%, 20%, 10%, or 5% (by dry weight) of non-herbicide resistance polypeptide (also referred to herein as a "contaminating protein"). In the present invention, "herbicide resistance protein" is intended an EPSP synthase polypeptide disclosed herein. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity.

By "variants" is intended proteins or polypeptides having an amino acid sequence that is at least about 60%, 65%, about 70%, 75%, about 80%, 85%, 90%, 91%, 92%, 93%, 94%, 95%, 96%, 97%, 98% or 99% identical to any of SEQ ID NO:7-28. One of skill in the art will recognize that these values can be appropriately adjusted to determine corresponding identity of polypeptides encoded by two polynucleotides by taking into account codon degeneracy, amino acid similarity, reading frame positioning, and the like.

For example, conservative amino acid substitutions may be made at one or more nonessential amino acid residues. A "nonessential" amino acid residue is a residue that can be altered from the wild-type sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or non-conserved alterations in the conserved residues.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

C. Polynucleotide Constructs

The polynucleotides encoding the EPSP synthase polypeptides of the present invention may be modified to obtain or enhance expression in plant cells. The polynucleotides encoding the polypeptides identified herein may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e., promoter, particularly a heterologous promoter) operably-linked to one or more polynucleotides of interest, and/or a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

"Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA*, 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of Chlorella virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO 97/41228); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.*, 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156). See also PCT WO 96/23898.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

D. Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

E. Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}P$ target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by grg sequences of the invention is then tested by hybridizing the filter to a radioactive probe derived from a GDC by methods known in the art (Sambrook and Russell (2001) supra)

Western blot and biochemical assays and the like may be carried out on the transgenic plants to determine the presence of protein encoded by the herbicide resistance gene by standard procedures (Sambrook and Russell (2001) supra) using antibodies that bind to one or more epitopes present on the herbicide resistance protein.

In one aspect of the invention, the grg genes described herein are useful as markers to assess transformation of bacterial or plant cells.

F. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, Brassica sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, hydrangea, hibiscus, roses, tulips, daffodils, petunias, carnation, poinsettia, and chrysanthemum. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

G. Methods for Increasing Plant Yield

Methods for increasing plant yield are provided. The methods comprise introducing into a plant or plant cell a polynucleotide comprising a grg sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant is treated with an effective concentration of an herbicide, where the herbicide application results in enhanced plant yield. By "effective concentration" is intended the concentration which allows the increased yield in the plant. Such effective concentrations for herbicides of interest are generally known in the art. The herbicide may be applied either pre- or post emergence in accordance with usual techniques for herbicide application to fields comprising crops which have been rendered resistant to the herbicide by heterologous expression of a grg gene of the invention.

Methods for conferring herbicide resistance in a plant or plant part are also provided. In such methods, a grg polynucleotide disclosed herein is introduced into the plant, wherein expression of the polynucleotide results in glyphosate tolerance or resistance. Plants produced via this method can be treated with an effective concentration of an herbicide and display an increased tolerance to the herbicide. An "effective concentration" of an herbicide in this application is an amount sufficient to slow or stop the growth of plants or plant parts that are not naturally resistant or rendered resistant to the herbicide.

H. Methods of Controlling Weeds in a Field

Methods for selectively controlling weeds in a field containing a plant are also provided. In one embodiment, the plant seeds or plants are glyphosate resistant as a result of a grg polynucleotide disclosed herein being inserted into the plant seed or plant. In specific methods, the plant is treated with an effective concentration of an herbicide, where the herbicide application results in a selective control of weeds or other untransformed plants. By "effective concentration" is intended the concentration which controls the growth or spread of weeds or other untransformed plants without significantly affecting the glyphosate-resistant plant or plant seed. Such effective concentrations for herbicides of interest are generally known in the art. The herbicide may be applied either pre- or post emergence in accordance with usual techniques for herbicide application to fields comprising plants or plant seeds which have been rendered resistant to the herbicide.

I. Temperature Spectrum

Several studies of glyphosate metabolism in plants have been carried out, and reveal that glyphosate is not metabolized by plants or is metabolized very slowly. Glyphosate penetrates the cuticle rapidly, and is translocated throughout plants over a considerable period of time (reviewed in Kearney and Kaufman, Eds (1988) *Herbicides; Chemistry, Degradation & Mode of Action* Marcel Dekker, Inc., New York, 3:1-70 and Grossbard and Atkinson, Eds. (1985) *The Herbicide Glyphosate* Butterworths, London, p. 25-34). Thus, it is likely that glyphosate tolerance is necessary over a sustained period of time following glyphosate exposure in agronomically-important plants. Where temperatures frequently exceed 30° C. during the growing season, it would be advantageous to employ a glyphosate-tolerance EPSP synthase that maintains activity at elevated temperatures.

In one embodiment of the present invention, the EPSP synthase exhibits thermal stability at a temperature that is higher or lower than ambient environmental temperature. By "thermal stability" is intended that the enzyme is active at a higher or lower temperature than ambient environmental temperature for a longer period of time than an EPSP synthase that is not thermal stable at that temperature. For example, a thermal stable EPSP synthase has enzymatic activity for greater than about 1 hour, greater than about 2 hours, about 3, about 4, about 5, about 6, about 7, about 8, about 9, about 10, about 11, about 12, about 13, about 14, about 15, about 20, about 25 hours, or longer, at a temperature that is higher or lower than ambient environmental temperature. For the purposes of the present invention, "ambient" environmental temperature is about 30° C. In some embodiments, a higher than ambient temperature is a temperature at or above about 32° C., about 34° C., about 37° C., about 40° C., about 45° C., about 50° C., about 55° C., about 60° C., about 65° C., or higher. A lower than ambient temperature is a temperature at or below about 28° C., below about 27° C., about 26° C., about 25° C., about 23° C., about 20° C., about 18° C., about 15° C., about 10° C., at or below about 5° C., or around 0° C. Methods to assay for EPSP synthase activity are discussed in further details elsewhere herein. For the purposes of the present invention, a thermal stable EPSP synthase is considered active when it functions at about 90% to 100%, about 80% to about 90%, about 70% to about 80%, about 60% to about 70% or about 50% to about 60% of the maximum activity level observed at the optimum temperature for that enzyme.

Thus, provided herein are methods and compositions for increasing glyphosate tolerance at temperatures higher than ambient environmental temperatures. In one embodiment, the methods comprise introducing into a plant a nucleotide sequence encoding the glyphosate tolerance EPSP synthase enzyme set forth in any of SEQ ID NO:7-28, and growing the plant at a temperature that is higher than ambient environmental temperature. In specific embodiments, the growing temperature is higher than ambient temperature for an average of at least about 2 hours per day, at least about 3 hours per day, at least about 4 hours per day, at least about 5, about 6, about 7, about 8, about 9, about 10, about 11, about 12, about 14, about 16, about 18, about 20, at least about 22 hours per day, or up to about 24 hours a day during the growing season of the plant.

In another embodiment, the method comprises introducing into a plant a nucleotide sequence encoding the glyphosate tolerant EPSP synthase enzyme set forth in any of SEQ ID NO:7-28, contacting the plant with an herbicidally-effective concentration of glyphosate, and growing the plant at a temperature that exceeds ambient environmental temperature for at least 1 hour, at least about 2 hours, at least about 3, at least about 4, or more hours per day for at least 2, 3, 4, 5, 6, 7, 8, 9, 10, 11, 12, 13, 14, 15, 16, 17, 18, 19, 20 or more days after glyphosate is applied to the plant, wherein the days in which the temperature exceeds ambient environmental temperature occur during the growing season of the plant.

The following examples are offered by way of illustration and not by way of limitation.

EXPERIMENTAL

Example 1

Q-Loop Coordinates of GRG31

U.S. patent application Ser. No. 11/651,752, filed Jan. 10, 2007 (herein incorporated by reference) discloses the Q-loop as an important region in conferring glyphosate resistance to EPSP synthases. The Q-loop is defined as the region from the alanine corresponding to amino acid position 81 of SEQ ID NO:5 (GRG1) to the leucine corresponding to amino acid position 102 of SEQ ID NO:5, where the "core" of the Q-loop is defined as amino acid positions 84 through 99 of SEQ ID NO:5.

Herein a position number is assigned to the amino acids in this core region to simplify referral to each amino acid residue in this region. Thus, the positions of the Q-loop core for GRG31 (I-D-I-G-P-A-G-T-A-M-R-F-L-T-A-Y) correspond to amino acids 73 through 88 of GRG31 (SEQ ID NO:2) and are herein designated as follows:

TABLE 1

Designation of Position Coordinates for Q-loop Core amino acids

| Amino Acid in GRG1 (SEQ ID NO: 5) (single letter code) | Amino Acid in GRG31 (SEQ ID NO: 2) (single letter code) | Designated Position in Q-loop core |
|---|---|---|
| I | I73 | Position 1 |
| D | D74 | Position 2 |
| C | I75 | Position 3 |
| G | G76 | Position 4 |
| E | P77 | Position 5 |
| S | A78 | Position 6 |
| G | G79 | Position 7 |
| L | T80 | Position 8 |
| S | A81 | Position 9 |
| I | M82 | Position 10 |
| R | R83 | Position 11 |
| M | F84 | Position 12 |
| F | L85 | Position 13 |
| T | T86 | Position 14 |
| P | A87 | Position 15 |
| I | Y88 | Position 16 |

Example 2

Syngrg31 Design and Expression

A novel gene sequence encoding the GRG31 protein (U.S. patent application Ser. No. 11/760,570, filed Jun. 8, 2007, herein incorporated by reference in its entirety) was designed and synthesized. This sequence is provided herein as SEQ ID NO:6. This open reading frame, designated "syngrg31" herein, was cloned into the expression vector pRSF1b (Invitrogen), by methods known in the art.

Example 3

Site Directed Mutagenesis of GRG31

U.S. patent application Ser. No. 11/762,580, filed Jun. 13, 2008, herein incorporated by reference in its entirety, describes methods for generating diversity. This method is referred to herein as "Permutational Mutagenesis." A permutational library for GRG31 was designed using the Q-loop diversity present in other glyphosate resistant EPSPS enzymes A glyphosate growth screen was developed. It was found that BL21*DE3 cells containing a GRG31 expression construct (pAX1945; GRG31 in pRSF1b) grow on agar plates (1×M63 minimal medium; 0.05 mM IPTG; 50 ug/ml Kanamycin) containing up to 50 mM glyphosate. Library 1 was cloned into pAX1945 between the MfeI and AlwN1 restriction sites.

Clone pAX3625 contains a grg31 variant having an in-frame stop codon that disrupts the GRG31 open reading frame. Thus, pAX3625 does not confer resistance to glyphosate. pAX3625 was utilized as a vector for the subsequent cloning and screening of the GRG31 libraries, since E. coli cells containing pAX3625 will not grow on glyphosate containing agar plates unless the Q-loop cassette of pAX3625 has been replaced with a glyphosate resistant Q-loop.

Library 1 was cloned into pAX3625 and 130,000 clones were plated onto plates containing 50 mM glyphosate. After 1.5 days, thirty-one (31) glyphosate resistant clones were selected as growing on glyphosate plates. Extracts were prepared and assessed for glyphosate resistance by assaying activity in the presence of a small number of glyphosate concentrations (0, 1, and 2 mM glyphosate). Six clones were identified as having the best activity in this prescreen; GRG31pm3a11, GRG31pm3a6, GRG31pm3a8, GRG31pm3b8, GRG31pm3b9, and GRG31pm3d3 (SEQ ID NO:7, 8, 9, 10, 11, and 12, respectively)

These clones share an isoleucine to cysteine substitution at position 3 of the Q-loop. Interestingly, GRG1 also contains a cysteine at this position. Extracts from these six clones were assayed for activity at a range of PEP concentrations (0, 20, 50, and 100 µM PEP). Clones 3a11 and 3b8 showed the best activity at low PEP concentrations and were purified. Clone 3b8 showed an improved $K_i$ (116 µM) relative to wild-type GRG31.

TABLE 2

Amino acid changes in clone 3b8

| Clone | Amino Acid Change(s) |
|---|---|
| 3b8 | I75→C; P77→N; M82→T; |

Example 4

GRG31 Library 3

Four Q-loop positions (positions 5, 9, 10, and 16), identified as capable of accepting variation, were selected to be randomized in a combinatorial library. This library was designated library 3.

Library 3 was cloned into pAX3625, unselected clones were sequenced and the library was found to have incorporated the indicated diversity.

One hundred and fifteen thousand (115,000) clones were plated onto plates containing 50 mM glyphosate and 384 glyphosate resistant clones were picked for sequencing. Sequencing of the Q-loop regions of these clones identified fifty-three (53) unique sequences. A $K_i$ assessment of the unique clones was carried out by testing activity at 0 and 0.2 mM glyphosate. From this assessment, nine (9) clones with the highest indication of increased resistance to glyphosate were identified. An assessment of the $K_m$ of protein encoded by these nine clones was performed by comparing activity at 0, 20, and 50 µM PEP. These assessments identified clones L3P2b11 (SEQ ID NO:13) and L3P2c11 (SEQ ID NO:14) as having the best combination of glyphosate resistance and activity at low PEP concentrations. Clone L3P2d11 (SEQ ID NO:15) was also selected for further study. L3P2c11 contains a single amino acid change (Y88-F) at position 16 of the Q-loop.

TABLE 3

Amino Acid changes in GRG31 variants

| Clone | Amino Acid Change(s) |
|---|---|
| L3P2b11 | P77→Q; A81→S; M82→L Y88→F |
| L3P2c11 | Y88→F |
| L3P2d11 | M82→F; Y88→L |

Example 5

GRG31 Library 4

A permutational library designated as Library 4 was generated, and cloned into pAX3625. Thirty-five thousand (35,000) clones were plated onto 50 mM glyphosate, and twenty-three (23) unique clones were identified from the set of clones that were screened. Extracts from those twenty-three clones were prepared and subjected to a $K_i$ assessment by testing the activity of their encoded proteins at 0, 0.2, and 0.5 mM glyphosate. Nine clones were selected, and the $K_m$ of their encoded proteins assessed at 0, 20, and 50 µM PEP. Clone L4e11 (SEQ ID NO:16) was identified as a clone with favorable properties in these tests. L4e11 protein was purified and its kinetic properties determined. The kinetics of L4e11 compared to other GRG31 variants described herein is shown in Table 5.

Example 6

Isolation of GRG31 Variant L5e3

Unique clones capable of conferring resistance to 50 mM glyphosate were isolated from a library of GRG31 variants in which Q-loop positions 2, 3, 4, 5, 6, 7, 9, 10, 14, 15, and 16 were mutagenized. These variants were tested for $K_m$ and $K_i$ as for previous libraries, and several clones were subjected to more detailed kinetic characterization. One such clone, L5E3 (SEQ ID NO:17), has a single amino acid change of the proline at amino acid 77 of GRG31 to a threonine. This amino acid alteration corresponds to position 5 of the Q-loop as per Table 1.

TABLE 4

Amino Acid changes in GRG31 variants

| Clone | Amino Acid Change(s) |
|---|---|
| L4e11 | I75→C; A78→S; Y88→H |
| L5e3 | P77→T |

Example 7

Kinetic Analysis of GRG31 Variants

GRG31 variants L3P2b11, L3P2c11 and L4e11, and L5e3 were characterized by enzymatic assays as described herein, and compared to the native GRG31 enzyme. For each enzyme the apparent $K_m$ ($K_{m(app)}$) was determined at each of several glyphosate concentrations, and a plot of $K_{m(app)}$ vs. glyphosate concentration was used to calculate the $K_i$ for each enzyme. The thermostability for each enzyme was assessed by incubating the enzyme at 37° C. for 16 hours, and then quantifying the enzymatic activity remaining (as $V_{max}$) vs. control enzyme that was incubated at 4° C.

Kinetic analysis reveals that clones L3P2b11, L3P2c11 and L4e11 have improved kinetic properties over GRG31, as shown in Table 5.

TABLE 5

Kinetics of L4e11 compared to other GRG31 variants

|  | GRG31 | L3P2b11 | L3P2c11 | L4e11 | L5e3 |
|---|---|---|---|---|---|
| $K_i$ (µM) | 73 | 983 | 715 | 389 | 507 |
| $K_m$ (µM) | 23 | 11 | 39.6 | 12.4 | 11.4 |
| $V_{max}$ | 29.3 | 5.7 | 5.3 | 3.5 | 3.6 |

TABLE 6

Location of Q-loop alterations in GRG31 variants

| Position in Q-loop | Amino Acid in GRG31 | Pm3b8 | L3P2b11 | L3P2c11 | L3P2d11 | L4e11 | L5e3 |
|---|---|---|---|---|---|---|---|
| Position 1 | I73 | — | — | — | — | — | — |
| Position 2 | D74 | — | — | — | — | — | — |
| Position 3 | I75 | C | — | — | — | C | — |
| Position 4 | G76 | — | — | — | — | — | — |
| Position 5 | P77 | N | Q | — | — | — | T |
| Position 6 | A78 | — | — | — | — | S | — |
| Position 7 | G79 | — | — | — | — | — | — |
| Position 8 | T80 | — | — | — | — | — | — |
| Position 9 | A81 | — | S | — | — | — | — |
| Position 10 | M82 | T | L | — | F | — | — |
| Position 11 | R83 | — | — | — | — | — | — |
| Position 12 | F84 | — | — | — | — | — | — |
| Position 13 | L85 | — | — | — | — | — | — |
| Position 14 | T86 | — | — | — | — | — | — |
| Position 15 | A87 | — | — | — | — | — | — |
| Position 16 | Y88 | — | F | F | L | H | — |

Clones L3P2b11, L3P2c11 and L4e11 showed an improved $K_i$ relative to GRG31.

Inspection of Table 6 illustrates that each of the Q-loop variants of GRG31 with improved kinetic properties have either a mutation in position 16, with a preference to mutation to phenylalanine at this position, or a mutation in position 5. Each of the mutations in Table 6 has a greatly improved $K_i$, and an improved $K_m$ for phophoenolpyruvate (PEP). This observation is consistent with the mechanism of resistance in these variants being due at least in part to improved binding affinity for PEP. PEP is subject to competitive inhibition by glyphosate, and improved PEP affinity will lead to a reduction in the $K_m$ apparent in the presence of glyphosate, and thus a higher $K_i$. Interestingly, each of these clones has a reduced $V_{max}$ relative to GRG31, consistent with the observation that alterations in this region can disrupt protein folding. However, the $V_{max}$ observed for these proteins is still sufficient for these proteins to confer resistance to high glyphosate concentrations upon E. coli cells. If one desired an improved $V_{max}$ for these variants, one could perform mutagenesis and screening strategies as provided herein, including regions outside the Q-loop, and select variants that exhibit improved $V_{max}$. Such strategies have proved effective for similar EPSP synthases (see U.S. patent application Ser. No. 11/762,526, filed Jun. 13, 2007, herein incorporated by reference in its entirety). Alternatively one can produce mutations that improve the folding and/or thermostability of an EPSPS such as the GRG31 protein, and then combine these mutations and test for variants with the improved binding properties of variants such as L3P2b11, L3P2c11, L3P2d11, L4e11, and or L5e3, but with further improvements in $V_{max}$.

Example 8

Development of Variants with Improved Thermostability

To improve the thermostability of GRG31, error prone PCR mutagenesis of GRG31 was performed. Forty-five thousand (45,000) clones were plated onto 50 mM glyphosate, and ninety-five (95) clones were picked. Extracts were prepared and tested for increased thermostability. Two clones (6b2, SEQ ID NO:18, and 6e7, SEQ ID NO:19) were identified as having increased thermostability. Sequencing showed that clone 6b2 contains two mutations (N95S and A206V), while clone 6e7 contains 1 mutation (E215K) relative to GRG31.

TABLE 7

Amino Acid Changes in GRG31 variants with improved thermostability

| Clone | Amino Acid Change(s) |
|---|---|
| 6b2 | N95→S, A206→V |
| 6e7 | E215→K |

Molecular modeling indicates that these three mutated positions are located on the surface of GRG31.

To further investigate the contributions of various substitutions in these positions, several point mutations were generated at positions corresponding to amino acid positions 95, 206, and 215 of GRG31. Extracts of point mutants were tested for thermostability at 37° C.:

TABLE 8

Thermostability of GRG31 variants

| Amino Acid Change(s) | Percent of Wt GRG31 activity (4 hrs at 37° C.) |
|---|---|
| N95→S, A206→V | 228% |
| E215→K | 213% |
| N95→S | 229% |
| N95→Q | 170% |
| A206→V | 213% |
| A206→S | 121% |
| E215→Q | 276% |

In a separate experiment, further residue changes were analyzed.

TABLE 9

Thermostability of GRG31 variants

| Amino Acid Change(s) | Percent of Wt GRG31 activity (4 hrs at 37° C.) |
|---|---|
| N95→S, A206→V | 139% |
| E215→K | 152% |
| N95→E | 48% |
| N95→D | 57% |
| N95→T | 118% |
| A206→R | 104% |
| A206→Q | 123% |
| A206→E | 152% |
| A206→T | 157% |
| E215→R | 118% |
| E215→S | 143% |
| E215→T | 111% |

The data indicates that the point mutations N95S and A206V can both contribute to increased thermostability.

Three variants (6b2, 6e7, and the triple EK (N95S A206V E215K; SEQ ID NO:20)) were grown, their proteins purified, and the thermostability of the proteins analyzed in more detail. The data (Table 10) indicates that variants 6b2, 6e7 as well as the triple mutant have increased thermostability compared to wild-type GRG31.

TABLE 10

Thermostability of GRG31 variants

| | GRG31 | 6e7 | 6b2 | Triple EK |
|---|---|---|---|---|
| Thermostability (4 hrs at 37° C.) | ++ | +++ | +++ | +++ |

Example 9

Kinetics of GRG31 Variants

The kinetic properties of the 6e2, 6b2 and Triple EK variants were also determined using the purified protein, and the solubility of the proteins was tested. The results are shown in Table 11. All three variants 6e7, 6b2, and Triple EK, encode proteins with improved (lower) $K_m$ for PEP relative to GRG31. Furthermore, 6e7 also has an improved $V_{max}$.

TABLE 11

KineticProperties of GRG31 variants

| | GRG31 | 6e7 | 6b2 | Triple EK |
|---|---|---|---|---|
| $K_i$ (μM) | 73 | 111 | 92 | 48.2 |
| $K_m$ (μM) | 23 | 3.4 | 6.5 | 7.2 |
| $V_{max}$ | 29.3 | 62 | 34 | 33 |

Clone 6e7 is notable in that it has a $V_{max}$ improvement of 2-fold over GRG31. Thus, these improved clones may be suitable for combination with other variants that have improvements in other kinetic properties such as $K_m$ for PEP or $K_i$ with respect to glyphosate.

Example 10

Combining Thermostability Improvements with Kinetic Improvements

GRG31 variants were designed that incorporated the thermostability improvement mutations identified in 6e7, 6b2 and Triple EK mutations into the L3P2b11 or L3P2c11 variants. L3P2c11+6e7 (SEQ ID NO:21) encodes a protein with 2 changes relative to GRG31 as shown in Table 12. L3P2b11+6e7 (SEQ ID NO:22) encodes a protein with 5 changes relative to GRG31 as shown in Table 12. L3P2c11+triple EK (SEQ ID NO:23) encodes a protein with 4 changes relative to GRG31 as shown in Table 12. L3P2b11+triple EK (SEQ ID NO:24) encodes a protein with 7 changes relative to GRG31 as shown in Table 12. L3P2c11+6b2 (SEQ ID NO:25) encodes a protein with 3 changes relative to GRG31 as shown in Table 12. L3P2b11+6b2 (SEQ ID NO:26) encodes a protein with 6 changes relative to GRG31 as shown in Table 12.

TABLE 12

Amino Acid changes in GRG31 Variants

| Clone | Amino Acid Change(s) |
|---|---|
| L3P2c11 + 6e7 | Y88→F; E215→K |
| L3P2b11 + 6e7 | P77→Q; A81→S; M82→L Y88→F; E215→K |
| L3P2c11 + triple EK | Y88→F; N95→S, A206→V; E215→K |
| L3P2b11 + triple EK | P77→Q; A81→S; M82→L Y88→F; N95→S, A206→V; E215→K |
| L3P2c11 + 6b2 | Y88→F; N95→S, A206→V |
| L3P2b11 + 6b2 | P77→Q; A81→S; M82→L Y88→F; N95→S, A206→V |

TABLE 13

Kinetics of GRG31 variants

| | GRG31 | L3P2c11 + 6e7 | L3P2b11 + 6e7 | L3P2c11 + triple EK | L3P2b11 + triple EK | L3P2c11 + 6b2 | L3P2b11 + 6b2 |
|---|---|---|---|---|---|---|---|
| $K_i$ (μM) | 73 | 416 | 1013 | 298 | 606 | 405 | 628 |
| $K_m$ (μM) | 23 | 8.6 | 10.3 | 12.6 | 12.3 | 7.9 | 8 |
| $V_{max}$ | 29.3 | 23.5 | 0.86 | 14.4 | 0.72 | 23.4 | 0.59 |

Table 13 shows that the variants with combined mutations have properties that are superior to the variants with either single set of alterations.

The variants GRG31(L3P2c11+6e7) and GRG31 (L3P2c11+6b2) exhibit more than four-fold improvement in $K_i$ for glyphosate, an approximately two-fold improvement in $K_m$ for PEP, and a $V_{max}$ that is approximately equal to that of GRG31, and is about four to five-fold improved over the GRG31(L3P2c11) protein.

Example 11

Thermostability of GRG31 Variants

The thermostability of several variants of GRG31 was analyzed by measuring survival of activity at 37° C. While L3P2c11+triple EK showed thermostability equivalent to GRG31, both L3P2c11+6b2 and L5E3 showed improved thermostability. Thus, these two clones have improved properties of higher $K_i$ for glyphosate, and improved thermostability at 37° C.

TABLE 14

Half-life of GRG31 variants at 37° C.

| | GRG31 | L5E3 | L3P2c11 + triple EK | L3P2c11 + 6b2 |
|---|---|---|---|---|
| $t_{1/2}$ at 37° C. (hours) | 2.7 | 10.8 | 2.7 | 3.5 |

Example 12

Improvement of GRG36

A gene encoding GRG36 (SEQ ID NO:4) that was optimized for plant expression (termed "syngrg36" and set forth in U.S. patent application Ser. No. 11/769,327, filed Jun. 27, 2007) was cloned into the plant transformation plasmid pAG3532. This plasmid was used as a template for error-prone PCR using the Mutazyme II system (Stratagene) to introduce random mutations into syngrg36. The template was diluted 1:50 in the error-prone PCR reaction, and amplification was carried out for 30 cycles. Individual PCR primers that flanked syngrg36 in this vector (T7 promoter, T7 terminator) were used. PCR product was digested with BamH I and Sgs I in Tango buffer, gel-purified, and ligated into the bacterial expression vector pRSF-1b vector to create a mutagenized grg36 library.

The syngrg36 DNA library was transformed into E. coli strain BL21*DE3 star (Invitrogen) for induction of protein expression. Following transformation, individual colonies were plated on 1×M63 medium containing 25 mM glyphosate to select for clones that had retained enzymatic activity and growth tolerance. Individual colonies were picked and arrayed into 384-well plates to create a mutagenized library for enzymatic activity screening. Two 384-well plates were created in this manner. Enzymatic activity screening was carried out as follows. Library clones were pinned into 96-well blocks containing LB medium and were grown to A600=0.6. IPTG was then added (0.5 mM) and the blocks were incubated overnight at 20° C. to induce protein expression. Next, protein extracts were prepared from individual cultures using POPCULTURE® reagent (Novagen) and the enzymatic activity was measured as disclosed in U.S. patent application Ser. No. 11/651,752, filed Jan. 10, 2007, herein incorporated by reference in its entirety. By this approach, 6 extracts were identified that possessed enzymatic activity that was 2 standard deviations higher than the average of wild-type GRG36 samples that were tested alongside. Each of these clones was DNA sequenced, and each was found to carry mutations in GRG36. These 6 were selected for further characterization.

Each of the 6 improved clones was grown and induced in 250 mL LB cultures. Following induction, each GRG36 protein variant was purified by affinity chromatography to a cobalt resin (Novagen). The purified proteins were tested for enzymatic activity following heating for 0, 4 and 6 hours at 37° C. One of the GRG36 protein variants, termed GRG36 (ace7) (SEQ ID NO:27) and encoded by syngrg36(ace7) (SEQ ID NO:29), was found to possess 7.5-fold higher thermostability at 37° C. than the wild-type GRG36 enzyme. A second GRG36 protein variant, termed GRG36(ace8) (SEQ ID NO:28) and encoded by syngrg36(ace8) (SEQ ID NO:30), was found to possess 2.5-fold higher thermostability than wild-type GRG36. These results are summarized in Table 15:

TABLE 15

Half-life of GRG36 enzymes at 37° C.

| Enzyme | Half-life at 37° C. |
|---|---|
| GRG36 | 2.5 hours |
| GRG36(ace7) | 18.8 hours |
| GRG36(ace8) | 7.3 hours |

Additionally, enzymatic assays were carried out to calculate the kinetic constants for substrate binding affinity ($K_m$), glyphosate binding ($K_i$) and enzymatic rate ($V_{max}$). Briefly, each enzyme was titrated with the substrate phosphoenolpyruvate and the linear enzymatic rate was plotted versus the substrate concentration. This plot was fit to the Michaelis-Menton equation to calculate the substrate concentration that produced one-half of the maximal rate ($K_m$), and the maximal rate obtained at saturating substrate was divided by the enzyme concentration to yield $V_{max}$. Next, additional substrate titrations were carried out at various glyphosate concentrations, and the apparent binding constant at each glyphosate concentration ($K_{obs}$) was plotted against the glyphosate concentration to yield a straight line. The $K_i$ was measured as (−)x-intercept. For the enzyme GRG36(ace7), a full $K_i$ measurement was not carried out, but very similar activity was observed between GRG36 and GRG36(ace7) at 1 mM glyphosate, suggesting that the two enzymes possess similar glyphosate binding properties.

TABLE 16

Kinetic values for GRG36 enzymes.

| Enzyme | $V_{max}$ (nmol/min/µg) | $K_m$ (µM) | $K_i$ (µM) |
|---|---|---|---|
| GRG36 | 8 | 6.3 | 421 |
| GRG36(ace7) | 1.8 | 9.8 | not measured |
| GRG36(ace8) | 6.8 | 11.03 | 435 |

Example 13

Cloning of grg Variants into a Plant Expression Cassette

For each of the grg variants described herein, the open reading frame (ORF) is amplified by PCR from a full-length DNA template. Hind III restriction sites are added to each end of the ORFs during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic*

Acids Research 15:6643-6653). The PCR product is cloned and sequenced using techniques well known in the art to ensure that no mutations are introduced during PCR.

The plasmid containing the PCR product is digested with Hind III and the fragment containing the intact ORF is isolated. This fragment is cloned into the Hind III site of a plasmid such as pAX200, a plant expression vector containing the rice actin promoter (McElroy et al. (1991) *Molec. Gen. Genet.* 231:150-160) and the PinII terminator (An et al. (1989) *The Plant Cell* 1:115-122). The promoter—gene—terminator fragment from this intermediate plasmid is then subcloned into plasmid pSB11 (Japan Tobacco, Inc.) to form a final pSB11-based plasmid. In some cases, it may be preferable to generate an alternate construct in which a chloroplast leader sequence is encoded as a fusion to the N-terminus of the grg constructs. These pSB11-based plasmids are typically organized such that the DNA fragment containing the promoter—gene—terminator construct, or promoter-chloroplast leader-gene-terminator construct may be excised by double digestion by restriction enzymes, such as Kpn I and Pme I, and used for transformation into plants by aerosol beam injection. The structure of the resulting pSB11-based clones is verified by restriction digest and gel electrophoresis, and by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plating on media containing spectinomycin. The pSB11-based plasmid clone carries spectinomycin resistance but is a narrow host range plasmid and cannot replicate in *Agrobacterium*. Spectinomycin resistant colonies arise when pSB11-based plasmids integrate into the broad host range plasmid pSB1 through homologous recombination. The cointegrate product of pSB1 and the pSB11-based plasmid is verified by Southern hybridization. The *Agrobacterium* strain harboring the cointegrate is used to transform maize by methods known in the art, such as, for example, the PureIntro method (Japan Tobacco).

Example 14

Transformation of Plant Cells by *Agrobacterium*-Mediated Transformation

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 ml/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 ml/L (of 1 mg/ml stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

| Materials DN62A5S Media | | |
|---|---|---|
| Components | per liter | Source |
| Chu's N6 Basal Salt Mixture (Prod. No. C 416) | 3.98 g/L | Phytotechnology Labs |
| Chu's N6 Vitamin Solution (Prod. No. C 149) | 1 ml/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 ml/L (of 1 mg/ml Stock) | Sigma |

Adjust the pH of the solution to pH 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 15

Transformation of EPSP Synthase Enzymes into Maize Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark.

However, it is not necessary per se to incubate the embryos overnight. Embryos are contacted with an *Agrobacterium* strain containing the appropriate vectors having an EPSP synthase enzyme of the present invention for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled

That which is claimed:

1. An isolated variant glyphosate tolerant EPSP synthase polypeptide comprising SEQ ID NO:2, wherein said variant is a substitution mutation of two or more amino acids in said SEQ ID NO:2 selected from the group consisting of:
   i) a cysteine residue at the position corresponding to amino acid position 75 of SEQ ID NO:2;
   ii) an aspartic acid residue at the position corresponding to amino acid position 76 of SEQ ID NO:2;
   iii) an asparagine, alanine, glutamine, or threonine residue at the position corresponding to amino acid position 77 of SEQ ID NO:2;
   iv) a serine residue at the position corresponding to amino acid position 78 of SEQ ID NO:2;
   v) a serine or glycine residue at the position corresponding to amino acid position 81 of SEQ ID NO:2;
   vi) a valine, threonine, leucine, or phenylalanine residue at the position corresponding to amino acid position 82 of SEQ ID NO:2;
   vii) an alanine residue at the position corresponding to amino acid position 86 of SEQ ID NO:2;
   viii) a glycine residue at the position corresponding to amino acid position 87 of SEQ ID NO:2;
   ix) a valine, leucine, or histidine residue at the position corresponding to amino acid position 88 of SEQ ID NO:2;
   x) a serine, or threonine residue at the position corresponding to amino acid position 95 of SEQ ID NO:2;
   xi) a serine, arginine, glutamine, glutamic acid, or threonine residue at the position corresponding to amino acid position 206 of SEQ ID NO:2; and
   xii) a lysine, glutamine, arginine, serine, or threonine residue at the position corresponding to amino acid position 215 of SEQ ID NO:2.

2. The isolated polypeptide of claim 1, wherein said polypeptide is selected from the group consisting of SEQ ID NO:7, 8, 9, 10, 11, 12, 13, 14, 15, 16, 17, 18, 19, 20, 21, 22, 23, 24, 25, and 26.

3. The polypeptide of claim 1 further comprising a heterologous amino acid sequence.

* * * * *

SEQUENCE LISTING

<160> NUMBER OF SEQ ID NOS: 30

<210> SEQ ID NO 1
<211> LENGTH: 1251
<212> TYPE: DNA
<213> ORGANISM: Sphingobacterium multivorum/faecium
<220> FEATURE:
<221> NAME/KEY: CDS
<222> LOCATION: (1)...(1251)

<400> SEQUENCE: 1

```
atg aat caa caa gtc atc acg ctg acg cat cct tca aaa aaa ata cag      48
Met Asn Gln Gln Val Ile Thr Leu Thr His Pro Ser Lys Lys Ile Gln
 1               5                  10                  15 ggt acg gtt caa ctc aca ggt tca aaa tct gag agc aac cgt gct ctt      96
Gly Thr Val Gln Leu Thr Gly Ser Lys Ser Glu Ser Asn Arg Ala Leu
                20                  25                  30 att atc cag tca ttg agc aaa gga caa gtt gaa ata gcc aac ctt tct     144
Ile Ile Gln Ser Leu Ser Lys Gly Gln Val Glu Ile Ala Asn Leu Ser
            35                  40                  45 gaa gct gca gat acg gta acg tta aac cgt gtg cta caa att gct tca     192
Glu Ala Ala Asp Thr Val Thr Leu Asn Arg Val Leu Gln Ile Ala Ser
        50                  55                  60 gat ccg aaa cca gga ttc aac aca att gac atc ggt cca gcg gga acg     240
Asp Pro Lys Pro Gly Phe Asn Thr Ile Asp Ile Gly Pro Ala Gly Thr
 65                  70                  75                  80 gcc atg cga ttc tta acg gct tac ctc aac ctt gtc aaa gga aat ttt     288
Ala Met Arg Phe Leu Thr Ala Tyr Leu Asn Leu Val Lys Gly Asn Phe
                 85                  90                  95 atc ctt aca ggt act gaa cgc atg caa cag cgt cct ata ggt ata tta     336
Ile Leu Thr Gly Thr Glu Arg Met Gln Gln Arg Pro Ile Gly Ile Leu
                100                 105                 110 gtt gat gcc atg aaa gaa att ggt gca gac atc cac tat gac aag aaa     384
Val Asp Ala Met Lys Glu Ile Gly Ala Asp Ile His Tyr Asp Lys Lys
            115                 120                 125 gtc gga tac cct cct ttg aaa att gag ggc ggg ctg ttt caa gaa aaa     432
Val Gly Tyr Pro Pro Leu Lys Ile Glu Gly Gly Leu Phe Gln Glu Lys
        130                 135                 140 gac cgt gtc aag att aaa ggt aat atc agc agc caa tat ata tca gcc     480
Asp Arg Val Lys Ile Lys Gly Asn Ile Ser Ser Gln Tyr Ile Ser Ala
145                 150                 155                 160 ctc tta tta att gca cct gca tta aaa aaa ggg ctt act tta gag att     528
Leu Leu Leu Ile Ala Pro Ala Leu Lys Lys Gly Leu Thr Leu Glu Ile
                165                 170                 175 gag ggt gaa tta acc tcc aga cct tat gta tca atg acc ttg gat atg     576
Glu Gly Glu Leu Thr Ser Arg Pro Tyr Val Ser Met Thr Leu Asp Met
                180                 185                 190 ctg aaa agt gtc ggg att cag cat gaa tgg aaa aac aat gcg att aaa     624
Leu Lys Ser Val Gly Ile Gln His Glu Trp Lys Asn Asn Ala Ile Lys
            195                 200                 205 att gcg ccg cag gca ttt gag aaa caa aca ata tat gtc gag cca gat     672
Ile Ala Pro Gln Ala Phe Glu Lys Gln Thr Ile Tyr Val Glu Pro Asp
        210                 215                 220 tgg agc gct gct tcc tat tgg tac gct atc gcc gca cta gca gat gca     720
Trp Ser Ala Ala Ser Tyr Trp Tyr Ala Ile Ala Ala Leu Ala Asp Ala
```

```
                    225                 230                 235                 240
aac gca tcg atc gta ttg ccc gga tta aga aaa aac agc tta cag ggt         768
Asn Ala Ser Ile Val Leu Pro Gly Leu Arg Lys Asn Ser Leu Gln Gly
                        245                 250                 255 gat att gct att ata agc att atg gag cat ttt ggt gta caa tcg agc         816
Asp Ile Ala Ile Ile Ser Ile Met Glu His Phe Gly Val Gln Ser Ser
                260                 265                 270 ttt gaa tcg gac gga tta cac tta aat aaa aag gta atc ggt tcg gat         864
Phe Glu Ser Asp Gly Leu His Leu Asn Lys Lys Val Ile Gly Ser Asp
            275                 280                 285 gta agc tta ttt aac ttt aaa gaa tgt ccc gat ctc gca caa act gta         912
Val Ser Leu Phe Asn Phe Lys Glu Cys Pro Asp Leu Ala Gln Thr Val
        290                 295                 300 gtt gtc gcg gct gcg tta aaa cga gat gta tct ttt acg ggc ttg             960
Val Val Val Ala Ala Ala Leu Lys Arg Asp Val Ser Phe Thr Gly Leu
305                 310                 315                 320 gag acc tta aaa att aag gag act gac cgt atc gcg gca cta caa aag        1008
Glu Thr Leu Lys Ile Lys Glu Thr Asp Arg Ile Ala Ala Leu Gln Lys
                325                 330                 335 gaa att gcg aaa ttt gga gcc gag cta att gaa gat ggc gat acc tac        1056
Glu Ile Ala Lys Phe Gly Ala Glu Leu Ile Glu Asp Gly Asp Thr Tyr
                340                 345                 350 cat ctg aaa aca gcg cag gta tat cag cct gaa gag gtt act ttc gat        1104
His Leu Lys Thr Ala Gln Val Tyr Gln Pro Glu Glu Val Thr Phe Asp
            355                 360                 365 act tac gaa gat cat cgc atg gcg atg gcg ttc gca cca ctg gca tta        1152
Thr Tyr Glu Asp His Arg Met Ala Met Ala Phe Ala Pro Leu Ala Leu
        370                 375                 380 gtt ttc gac cag att aag att gct gaa cct caa gtt gta gaa aaa tca        1200
Val Phe Asp Gln Ile Lys Ile Ala Glu Pro Gln Val Val Glu Lys Ser
385                 390                 395                 400 tat cct gat ttt tgg aat cat tta cag gcg caa gct ttt gtc att gaa        1248
Tyr Pro Asp Phe Trp Asn His Leu Gln Ala Gln Ala Phe Val Ile Glu
                405                 410                 415 tag                                                                    1251

<210> SEQ ID NO 2
<211> LENGTH: 416
<212> TYPE: PRT
<213> ORGANISM: Sphingobacterium multivorum/faecium

<400> SEQUENCE: 2

Met Asn Gln Gln Val Ile Thr Leu Thr His Pro Ser Lys Lys Ile Gln
 1               5                  10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Pro Ala Gly Thr
65                  70                  75                  80

Ala Met Arg Phe Leu Thr Ala Tyr Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125
```

```
Val Gly Tyr Pro Pro Leu Lys Ile Glu Gly Gly Leu Phe Gln Glu Lys
        130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 3
<211> LENGTH: 1344
<212> TYPE: DNA
<213> ORGANISM: Unknown
<220> FEATURE:
<223> OTHER INFORMATION: derived from organism isolated from soil
<221> NAME/KEY: CDS
<222> LOCATION: (1)...(1344)

<400> SEQUENCE: 3 atg aaa aat caa aat ttt gat gct aaa gcc cgt agc ccg tgg aca ccg      48
Met Lys Asn Gln Asn Phe Asp Ala Lys Ala Arg Ser Pro Trp Thr Pro
1               5                   10                  15 tta aaa ggt gta aat aag ata agt gtt tca cct agt aaa gga aga ata      96
Leu Lys Gly Val Asn Lys Ile Ser Val Ser Pro Ser Lys Gly Arg Ile
            20                  25                  30 aat gga acc gtt act att cct ggt agc aag agt tta acc aac aga gct     144
Asn Gly Thr Val Thr Ile Pro Gly Ser Lys Ser Leu Thr Asn Arg Ala
        35                  40                  45 tta atc ata agt tct cta gct agt gga aag tca aaa gtg caa ggt att     192
Leu Ile Ile Ser Ser Leu Ala Ser Gly Lys Ser Lys Val Gln Gly Ile
```

-continued

```
                50                       55                        60
tta aaa agc gat gat tca ttt tgg tgt tta gac tcc ttg aaa aag cta     240
Leu Lys Ser Asp Asp Ser Phe Trp Cys Leu Asp Ser Leu Lys Lys Leu
 65              70                      75                  80 gga gta aat gtg aaa att caa gga gat aca gct ttt atc gaa gga aac     288
Gly Val Asn Val Lys Ile Gln Gly Asp Thr Ala Phe Ile Glu Gly Asn
                     85                      90                  95 ggt ggt aaa tgg gaa tca ggt gat tta tat att ggt gca gca gga acg     336
Gly Gly Lys Trp Glu Ser Gly Asp Leu Tyr Ile Gly Ala Ala Gly Thr
            100                     105                 110 att gca cga ttt cta cct gga gca tta gca gtt tca ggt aca ggc ata     384
Ile Ala Arg Phe Leu Pro Gly Ala Leu Ala Val Ser Gly Thr Gly Ile
                115                     120                 125 tgg gag tta gaa gcc agt aaa agt atg agt aaa cga cct att tca ccc     432
Trp Glu Leu Glu Ala Ser Lys Ser Met Ser Lys Arg Pro Ile Ser Pro
        130                     135                 140 tta gta gat gct tta aaa gag ctt ggg gct gaa ata aca tat cta agc     480
Leu Val Asp Ala Leu Lys Glu Leu Gly Ala Glu Ile Thr Tyr Leu Ser
145                     150                     155                 160 gat caa ggc tac tat ccg ttg tta gtt aaa gga aaa caa cta aat ggg     528
Asp Gln Gly Tyr Tyr Pro Leu Leu Val Lys Gly Lys Gln Leu Asn Gly
                    165                     170                 175 ggc gag gtt gaa ctc tca ggt aga att tct agt cag ttt ata agt ggt     576
Gly Glu Val Glu Leu Ser Gly Arg Ile Ser Ser Gln Phe Ile Ser Gly
            180                     185                 190 cta ttg att gcc tcg cct tat tta aat gat cca atc aag att aat att     624
Leu Leu Ile Ala Ser Pro Tyr Leu Asn Asp Pro Ile Lys Ile Asn Ile
        195                     200                 205 aaa gat cac atc gtt caa cac tca tat gta ctc tta act ttg gaa tta     672
Lys Asp His Ile Val Gln His Ser Tyr Val Leu Leu Thr Leu Glu Leu
210                     215                     220 atg aaa aag ttt ggt gca aaa gtt aaa tac gat agt agc cta aaa gaa     720
Met Lys Lys Phe Gly Ala Lys Val Lys Tyr Asp Ser Ser Leu Lys Glu
225                     230                     235                 240 ata gtc gtc tat cca tct aag tac act cca caa gat ata aat tta gaa     768
Ile Val Val Tyr Pro Ser Lys Tyr Thr Pro Gln Asp Ile Asn Leu Glu
                    245                     250                 255 gca gat gtt tcc act gca tgt tat ttt ctg gct ctt gct gca gtg acc     816
Ala Asp Val Ser Thr Ala Cys Tyr Phe Leu Ala Leu Ala Ala Val Thr
            260                     265                 270 aac ggt aaa gta caa att gat aat cta act tat gaa aca aaa caa cca     864
Asn Gly Lys Val Gln Ile Asp Asn Leu Thr Tyr Glu Thr Lys Gln Pro
        275                     280                 285 gat ata aaa atg gtt gat atc ctt gaa cgg atg gga tgc aaa gta aca     912
Asp Ile Lys Met Val Asp Ile Leu Glu Arg Met Gly Cys Lys Val Thr
        290                     295                 300 aga ggt tct tca ttc att gaa ata gag gga gtt agt caa tta aaa ggt     960
Arg Gly Ser Ser Phe Ile Glu Ile Glu Gly Val Ser Gln Leu Lys Gly
305                     310                     315                 320 gga ttt gaa atc tct atg agg gaa atg tct gac caa gtg tta act cta    1008
Gly Phe Glu Ile Ser Met Arg Glu Met Ser Asp Gln Val Leu Thr Leu
                    325                     330                 335 gca gca att gct cca ttc gca gat gaa cca ata acc ata aaa gac gtt    1056
Ala Ala Ile Ala Pro Phe Ala Asp Glu Pro Ile Thr Ile Lys Asp Val
            340                     345                 350 gaa cat ata cgc cat cac gaa tca aat cga atc agt gta cta gtt gat    1104
Glu His Ile Arg His His Glu Ser Asn Arg Ile Ser Val Leu Val Asp
        355                     360                 365 tca cta tct agg tta gga att ata gta gaa gaa ttt aaa gat gga cta    1152
Ser Leu Ser Arg Leu Gly Ile Ile Val Glu Glu Phe Lys Asp Gly Leu
```

```
              370                 375                 380
aaa gtg tat ccg ggt aat ccg aaa gcc act tta cta gat aca cac gat    1200
Lys Val Tyr Pro Gly Asn Pro Lys Ala Thr Leu Leu Asp Thr His Asp
385                 390                 395                 400 gat cat aga gtt gca atg gca tta tca ctt ata ggt tca aga gtt gaa    1248
Asp His Arg Val Ala Met Ala Leu Ser Leu Ile Gly Ser Arg Val Glu
                405                 410                 415 ggt ata caa ata aat gat cca gga tgt gta tct aaa act tgt cct cag    1296
Gly Ile Gln Ile Asn Asp Pro Gly Cys Val Ser Lys Thr Cys Pro Gln
            420                 425                 430 tat ttt gaa tta ttg gaa aaa cta ggt ttg aat ata att aaa cat tga    1344
Tyr Phe Glu Leu Leu Glu Lys Leu Gly Leu Asn Ile Ile Lys His
        435                 440                 445

<210> SEQ ID NO 4
<211> LENGTH: 447
<212> TYPE: PRT
<213> ORGANISM: Unknown
<220> FEATURE:
<223> OTHER INFORMATION: derived from organism isolated from soil

<400> SEQUENCE: 4

Met Lys Asn Gln Asn Phe Asp Ala Lys Ala Arg Ser Pro Trp Thr Pro
 1               5                  10                  15

Leu Lys Gly Val Asn Lys Ile Ser Val Ser Pro Ser Lys Gly Arg Ile
            20                  25                  30

Asn Gly Thr Val Thr Ile Pro Gly Ser Lys Ser Leu Thr Asn Arg Ala
        35                  40                  45

Leu Ile Ile Ser Ser Leu Ala Ser Gly Lys Ser Lys Val Gln Gly Ile
    50                  55                  60

Leu Lys Ser Asp Asp Ser Phe Trp Cys Leu Asp Ser Leu Lys Lys Leu
65                  70                  75                  80

Gly Val Asn Val Lys Ile Gln Gly Asp Thr Ala Phe Ile Glu Gly Asn
                85                  90                  95

Gly Gly Lys Trp Glu Ser Gly Asp Leu Tyr Ile Gly Ala Ala Gly Thr
            100                 105                 110

Ile Ala Arg Phe Leu Pro Gly Ala Leu Ala Val Ser Gly Thr Gly Ile
        115                 120                 125

Trp Glu Leu Glu Ala Ser Lys Ser Met Ser Lys Arg Pro Ile Ser Pro
    130                 135                 140

Leu Val Asp Ala Leu Lys Glu Leu Gly Ala Glu Ile Thr Tyr Leu Ser
145                 150                 155                 160

Asp Gln Gly Tyr Tyr Pro Leu Leu Val Lys Gly Lys Gln Leu Asn Gly
                165                 170                 175

Gly Glu Val Glu Leu Ser Gly Arg Ile Ser Ser Gln Phe Ile Ser Gly
            180                 185                 190

Leu Leu Ile Ala Ser Pro Tyr Leu Asn Asp Pro Ile Lys Ile Asn Ile
        195                 200                 205

Lys Asp His Ile Val Gln His Ser Tyr Val Leu Leu Thr Leu Glu Leu
    210                 215                 220

Met Lys Lys Phe Gly Ala Lys Val Lys Tyr Asp Ser Ser Leu Lys Glu
225                 230                 235                 240

Ile Val Val Tyr Pro Ser Lys Tyr Thr Pro Gln Asp Ile Asn Leu Glu
                245                 250                 255

Ala Asp Val Ser Thr Ala Cys Tyr Phe Leu Ala Leu Ala Ala Val Thr
            260                 265                 270

Asn Gly Lys Val Gln Ile Asp Asn Leu Thr Tyr Glu Thr Lys Gln Pro
```

```
                275                 280                 285
Asp Ile Lys Met Val Asp Ile Leu Glu Arg Met Gly Cys Lys Val Thr
290                 295                 300

Arg Gly Ser Ser Phe Ile Glu Ile Glu Gly Val Ser Gln Leu Lys Gly
305                 310                 315                 320

Gly Phe Glu Ile Ser Met Arg Glu Met Ser Asp Gln Val Leu Thr Leu
                325                 330                 335

Ala Ala Ile Ala Pro Phe Ala Asp Glu Pro Ile Thr Ile Lys Asp Val
                340                 345                 350

Glu His Ile Arg His His Glu Ser Asn Arg Ile Ser Val Leu Val Asp
                355                 360                 365

Ser Leu Ser Arg Leu Gly Ile Ile Val Glu Glu Phe Lys Asp Gly Leu
        370                 375                 380

Lys Val Tyr Pro Gly Asn Pro Lys Ala Thr Leu Leu Asp Thr His Asp
385                 390                 395                 400

Asp His Arg Val Ala Met Ala Leu Ser Leu Ile Gly Ser Arg Val Glu
                405                 410                 415

Gly Ile Gln Ile Asn Asp Pro Gly Cys Val Ser Lys Thr Cys Pro Gln
                420                 425                 430

Tyr Phe Glu Leu Leu Glu Lys Leu Gly Leu Asn Ile Ile Lys His
        435                 440                 445

<210> SEQ ID NO 5
<211> LENGTH: 431
<212> TYPE: PRT
<213> ORGANISM: Enterobacteriaceae

<400> SEQUENCE: 5

Val Lys Val Thr Ile Gln Pro Gly Asp Leu Thr Gly Ile Ile Gln Ser
1               5                   10                  15

Pro Ala Ser Lys Ser Ser Met Gln Arg Ala Cys Ala Ala Ala Leu Val
                20                  25                  30

Ala Lys Gly Ile Ser Glu Ile Ile Asn Pro Gly His Ser Asn Asp Asp
            35                  40                  45

Lys Ala Ala Arg Asp Ile Val Ser Arg Leu Gly Ala Arg Leu Glu Asp
        50                  55                  60

Gln Pro Asp Gly Ser Leu Gln Ile Thr Ser Glu Gly Val Lys Pro Val
65                  70                  75                  80

Ala Pro Phe Ile Asp Cys Gly Glu Ser Gly Leu Ser Ile Arg Met Phe
                85                  90                  95

Thr Pro Ile Val Ala Leu Ser Lys Glu Glu Val Thr Ile Lys Gly Ser
                100                 105                 110

Gly Ser Leu Val Thr Arg Pro Met Asp Phe Phe Asp Glu Ile Leu Pro
        115                 120                 125

His Leu Gly Val Lys Val Lys Ser Asn Gln Gly Lys Leu Pro Leu Val
    130                 135                 140

Ile Gln Gly Pro Leu Lys Pro Ala Asp Val Thr Val Asp Gly Ser Leu
145                 150                 155                 160

Ser Ser Gln Phe Leu Thr Gly Leu Leu Leu Ala Tyr Ala Ala Ala Asp
                165                 170                 175

Ala Ser Asp Val Ala Ile Lys Val Thr Asn Leu Lys Ser Arg Pro Tyr
                180                 185                 190

Ile Asp Leu Thr Leu Asp Val Met Lys Arg Phe Gly Leu Lys Thr Pro
        195                 200                 205

Glu Asn Arg Asn Tyr Glu Glu Phe Tyr Phe Lys Ala Gly Asn Val Tyr
```

```
                210                 215                 220
Asp Glu Thr Lys Met Gln Arg Tyr Thr Val Glu Gly Asp Trp Ser Gly
225                 230                 235                 240

Gly Ala Phe Leu Leu Val Ala Gly Ala Ile Ala Gly Pro Ile Thr Val
                245                 250                 255

Arg Gly Leu Asp Ile Ala Ser Thr Gln Ala Asp Lys Ala Ile Val Gln
            260                 265                 270

Ala Leu Met Ser Ala Asn Ala Gly Ile Ala Ile Asp Ala Lys Glu Ile
            275                 280                 285

Lys Leu His Pro Ala Asp Leu Asn Ala Phe Glu Phe Asp Ala Thr Asp
        290                 295                 300

Cys Pro Asp Leu Phe Pro Pro Leu Val Ala Leu Ala Ser Tyr Cys Lys
305                 310                 315                 320

Gly Glu Thr Lys Ile Lys Gly Val Ser Arg Leu Ala His Lys Glu Ser
                325                 330                 335

Asp Arg Gly Leu Thr Leu Gln Asp Glu Phe Gly Lys Met Gly Val Glu
            340                 345                 350

Ile His Leu Glu Gly Asp Leu Met Arg Val Ile Gly Gly Lys Gly Val
            355                 360                 365

Lys Gly Ala Glu Val Ser Ser Arg His Asp His Arg Ile Ala Met Ala
        370                 375                 380

Cys Ala Val Ala Ala Leu Lys Ala Val Gly Glu Thr Thr Ile Glu His
385                 390                 395                 400

Ala Glu Ala Val Asn Lys Ser Tyr Pro Asp Phe Tyr Ser Asp Leu Lys
                405                 410                 415

Gln Leu Gly Gly Val Val Ser Leu Asn His Gln Phe Asn Phe Ser
            420                 425                 430

<210> SEQ ID NO 6
<211> LENGTH: 1251
<212> TYPE: DNA
<213> ORGANISM: Artificial Sequence
<220> FEATURE:
<223> OTHER INFORMATION: synthetic nucleotide sequence encoding GRG31
      protein (syngrg31)

<400> SEQUENCE: 6
atgaaccagc aggtgatcac cttgacacat ccaagcaaga agatccaagg caccgtgcag      60
ctcaccggca gcaagagcga gagcaacagg gcgctcatca ttcagagctt gagcaagggc     120
caagtggaga tcgccaacct tcagaagct  gctgacaccg tcaccctcaa cagggtgctg     180
caaattgctt cagatccaaa gcctggcttc aacaccatcg acattgggcc ggccggcacc     240
gccatgaggt tcttgacggc ctacctcaac ctggtgaagg caacttcat  cctcaccggc     300 actgaaagga tgcagcagcg gcccatcggc atcctggtgg acgccatgaa ggagatcggc     360
gccgacatcc actacgacaa gaaggtgggc tacccgccgc taaagattga aggaggcctc     420
ttccaagaga aggaccgcgt caagatcaag ggcaacatca gcagccagta catctcggcg     480
ctgctgctca tcgcgccggc gctgaagaag gggctgacgc tggagattga aggagagctg     540
acatcaaggc cttatgtgag catgacgctg gacatgctga agagcgtcgg catccagcat     600
gaatggaaga caacgccat  caagattgct cctcaagcat tgagaagca  gaccatctat     660 gtggagccag attggagcgc cgcctcatat tggtacgcca tcgccgcgct ggctgatgca     720
aatgcaagca tcgtgctgcc agggctgagg aagaacagcc tccaaggaga catcgccatc     780
atcagcatca tggagcattt tggagttcaa agttcatttg agagcgacgg cctccacctc     840
```

-continued

```
aacaagaagg tgattggaag tgatgtgagc ctcttcaact tcaaggagtg cccagatctt    900
gctcaaacag tggtggtggt ggcggcggcg ctgaagagag atgtgagctt caccggcctg    960
gagacgctga agatcaagga gaccgacagg atcgccgcgc tacagaagga gatcgccaag   1020
ttcggcgccg agctgattga agatgggaga acctaccacc tcaagacggc gcaggtgtac   1080
cagccagaag aagtcacctt cgacacctat gaagatcaca ggatggcaat ggccttcgcg   1140
ccgctagctc tggtgttcga ccagatcaag attgctgaac tcaagtggt ggagaagagc    1200
tacccggact tctggaacca cctccaagct caagccttcg tcatcgagta g            1251
```

<210> SEQ ID NO 7
<211> LENGTH: 416
<212> TYPE: PRT
<213> ORGANISM: Artificial Sequence
<220> FEATURE:
<223> OTHER INFORMATION: GRG31 variant (clone GRG31pm3a11)

<400> SEQUENCE: 7

```
Met Asn Gln Gln Val Ile Thr Leu Thr His Pro Ser Lys Lys Ile Gln
  1               5                  10                  15

Gly Thr Val Gln Leu Thr Gly Ser Lys Ser Glu Ser Asn Arg Ala Leu
             20                  25                  30

Ile Ile Gln Ser Leu Ser Lys Gly Gln Val Glu Ile Ala Asn Leu Ser
         35                  40                  45

Glu Ala Ala Asp Thr Val Thr Leu Asn Arg Val Leu Gln Ile Ala Ser
 50                  55                  60

Asp Pro Lys Pro Gly Phe Asn Thr Ile Asp Cys Gly Asn Ala Gly Thr
 65                  70                  75                  80

Ser Val Arg Phe Leu Thr Gly Phe Leu Asn Leu Val Lys Gly Asn Phe
                 85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300
```

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
            325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 8
<211> LENGTH: 416
<212> TYPE: PRT
<213> ORGANISM: Artificial Sequence
<220> FEATURE:
<223> OTHER INFORMATION: GRG31 variant (clone GRG31pm3a6)

<400> SEQUENCE: 8

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Cys Gly Asn Ala Gly Thr
65                  70                  75                  80

Ser Met Arg Phe Leu Thr Ala Val Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

-continued

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 9
<211> LENGTH: 416
<212> TYPE: PRT
<213> ORGANISM: Artificial Sequence
<220> FEATURE:
<223> OTHER INFORMATION: GRG31 variant (clone GRG31pm3a8)

<400> SEQUENCE: 9

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Cys Gly Pro Ala Gly Thr
65                  70                  75                  80

Gly Val Arg Phe Leu Thr Ala Phe Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp

```
                    210                 215                 220
Trp Ser Ala Ala Ser Tyr Trp Tyr Ala Ile Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
                260                 265                 270

Phe Glu Ser Asp Gly Leu His Leu Asn Lys Lys Val Ile Gly Ser Asp
                275                 280                 285

Val Ser Leu Phe Asn Phe Lys Glu Cys Pro Asp Leu Ala Gln Thr Val
290                 295                 300

Val Val Val Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
                340                 345                 350

His Leu Lys Thr Ala Gln Val Tyr Gln Pro Glu Glu Val Thr Phe Asp
                355                 360                 365

Thr Tyr Glu Asp His Arg Met Ala Met Ala Phe Ala Pro Leu Ala Leu
370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 10
<211> LENGTH: 416
<212> TYPE: PRT
<213> ORGANISM: Artificial Sequence
<220> FEATURE:
<223> OTHER INFORMATION: GRG31 variant (clone GRG31pm3b8)

<400> SEQUENCE: 10

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
                20                  25                  30

Ile Ile Gln Ser Leu Ser Lys Gly Gln Val Glu Ile Ala Asn Leu Ser
            35                  40                  45

Glu Ala Ala Asp Thr Val Thr Leu Asn Arg Val Leu Gln Ile Ala Ser
50                  55                  60

Asp Pro Lys Pro Gly Phe Asn Thr Ile Asp Cys Gly Asn Ala Gly Thr
65                  70                  75                  80

Ala Thr Arg Phe Leu Thr Ala Tyr Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175
```

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
                260                 265                 270

Phe Glu Ser Asp Gly Leu His Leu Asn Lys Lys Val Ile Gly Ser Asp
            275                 280                 285

Val Ser Leu Phe Asn Phe Lys Glu Cys Pro Asp Leu Ala Gln Thr Val
        290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 11
<211> LENGTH: 416
<212> TYPE: PRT
<213> ORGANISM: Artificial Sequence
<220> FEATURE:
<223> OTHER INFORMATION: GRG31 variant (clone GRG31pm3b9)

<400> SEQUENCE: 11

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Cys Asp Ala Ala Gly Thr
65                  70                  75                  80

Ser Met Arg Phe Leu Ala Ala Tyr Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
            130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 12
<211> LENGTH: 416
<212> TYPE: PRT
<213> ORGANISM: Artificial Sequence
<220> FEATURE:
<223> OTHER INFORMATION: GRG31 variant (clone GRG31pm3b3)

<400> SEQUENCE: 12

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Cys Asp Ala Ala Gly Thr
65                  70                  75                  80

Ala Thr Arg Phe Leu Thr Ala Phe Leu Asn Leu Val Lys Gly Asn Phe

```
              85                  90                  95
Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
            115                 120                 125

Val Gly Tyr Pro Pro Leu Lys Ile Glu Gly Gly Leu Phe Gln Glu Lys
            130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
            195                 200                 205

Ile Ala Pro Gln Ala Phe Glu Lys Gln Thr Ile Tyr Val Glu Pro Asp
            210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
            275                 280                 285

Val Ser Leu Phe Asn Phe Lys Glu Cys Pro Asp Leu Ala Gln Thr Val
            290                 295                 300

Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
            355                 360                 365

Thr Tyr Glu Asp His Arg Met Ala Met Ala Phe Ala Pro Leu Ala Leu
            370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 13
<211> LENGTH: 416
<212> TYPE: PRT
<213> ORGANISM: Artificial Sequence
<220> FEATURE:
<223> OTHER INFORMATION: GRG31 variant (clone L3P2b11)

<400> SEQUENCE: 13

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45
```

```
Glu Ala Ala Asp Thr Val Thr Leu Asn Arg Val Leu Gln Ile Ala Ser
 50                  55                  60

Asp Pro Lys Pro Gly Phe Asn Thr Ile Asp Ile Gly Gln Ala Gly Thr
 65                  70                  75                  80

Ser Leu Arg Phe Leu Thr Ala Phe Leu Asn Leu Val Lys Gly Asn Phe
                 85                  90                  95

Ile Leu Thr Gly Thr Glu Arg Met Gln Gln Arg Pro Ile Gly Ile Leu
                100                 105                 110

Val Asp Ala Met Lys Glu Ile Gly Ala Asp Ile His Tyr Asp Lys Lys
                115                 120                 125

Val Gly Tyr Pro Pro Leu Lys Ile Glu Gly Gly Leu Phe Gln Glu Lys
130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
                180                 185                 190

Leu Lys Ser Val Gly Ile Gln His Glu Trp Lys Asn Asn Ala Ile Lys
                195                 200                 205

Ile Ala Pro Gln Ala Phe Glu Lys Gln Thr Ile Tyr Val Glu Pro Asp
210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
                260                 265                 270

Phe Glu Ser Asp Gly Leu His Leu Asn Lys Lys Val Ile Gly Ser Asp
                275                 280                 285

Val Ser Leu Phe Asn Phe Lys Glu Cys Pro Asp Leu Ala Gln Thr Val
290                 295                 300

Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Leu Gln Lys
                325                 330                 335

Glu Ile Ala Lys Phe Gly Ala Glu Leu Ile Glu Asp Gly Asp Thr Tyr
                340                 345                 350

His Leu Lys Thr Ala Gln Val Tyr Gln Pro Glu Glu Val Thr Phe Asp
                355                 360                 365

Thr Tyr Glu Asp His Arg Met Ala Met Ala Phe Ala Pro Leu Ala Leu
                370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 14
<211> LENGTH: 416
<212> TYPE: PRT
<213> ORGANISM: Artificial Sequence
<220> FEATURE:
<223> OTHER INFORMATION: GRG31 variant (clone L3P2c11)

<400> SEQUENCE: 14
```

```
Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
50                  55                  60

Asp Pro Lys Pro Gly Phe Asn Thr Ile Asp Ile Gly Pro Ala Gly Thr
65              70                  75                  80

Ala Met Arg Phe Leu Thr Ala Phe Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 15
```

```
<211> LENGTH: 416
<212> TYPE: PRT
<213> ORGANISM: Artificial Sequence
<220> FEATURE:
<223> OTHER INFORMATION: GRG31 variant (clone L3P2d11)

<400> SEQUENCE: 15

Met Asn Gln Gln Val Ile Thr Leu Thr His Pro Ser Lys Lys Ile Gln
 1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
50                  55                  60

Asp Pro Lys Pro Gly Phe Asn Thr Ile Asp Ile Gly Pro Ala Gly Thr
65                  70                  75                  80

Ala Phe Arg Phe Leu Thr Ala Leu Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
370                 375                 380
```

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
            405                 410                 415

<210> SEQ ID NO 16
<211> LENGTH: 416
<212> TYPE: PRT
<213> ORGANISM: Artificial Sequence
<220> FEATURE:
<223> OTHER INFORMATION: GRG31 variant (clone 4e11)

<400> SEQUENCE: 16

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
50                  55                  60

Asp Pro Lys Pro Gly Phe Asn Thr Ile Asp Cys Gly Pro Ser Gly Thr
65                  70                  75                  80

Ala Met Arg Phe Leu Thr Ala His Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr

```
                    340                 345                 350
His Leu Lys Thr Ala Gln Val Tyr Gln Pro Glu Glu Val Thr Phe Asp
                355                 360                 365

Thr Tyr Glu Asp His Arg Met Ala Met Ala Phe Ala Pro Leu Ala Leu
            370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 17
<211> LENGTH: 416
<212> TYPE: PRT
<213> ORGANISM: Artificial Sequence
<220> FEATURE:
<223> OTHER INFORMATION: GRG31 variant (clone L5e3)

<400> SEQUENCE: 17

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Thr Ala Gly Thr
65                  70                  75                  80

Ala Met Arg Phe Leu Thr Ala Tyr Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300
```

Val Val Val Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
            325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 18
<211> LENGTH: 416
<212> TYPE: PRT
<213> ORGANISM: Artificial Sequence
<220> FEATURE:
<223> OTHER INFORMATION: GRG31 variant (clone 6b2)

<400> SEQUENCE: 18

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Pro Ala Gly Thr
65                  70                  75                  80

Ala Met Arg Phe Leu Thr Ala Tyr Leu Asn Leu Val Lys Gly Ser Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Val Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
                260                 265                 270

Phe Glu Ser Asp Gly Leu His Leu Asn Lys Lys Val Ile Gly Ser Asp
            275                 280                 285

Val Ser Leu Phe Asn Phe Lys Glu Cys Pro Asp Leu Ala Gln Thr Val
    290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
    355                 360                 365

Thr Tyr Glu Asp His Arg Met Ala Met Ala Phe Ala Pro Leu Ala Leu
370                 375                 380

Val Phe Asp Gln Ile Lys Ile Ala Glu Pro Gln Val Val Glu Lys Ser
                385                 390                 395                 400

Tyr Pro Asp Phe Trp Asn His Leu Gln Ala Gln Ala Phe Val Ile Glu
            405                 410                 415

<210> SEQ ID NO 19
<211> LENGTH: 416
<212> TYPE: PRT
<213> ORGANISM: Artificial Sequence
<220> FEATURE:
<223> OTHER INFORMATION: GRG31 variant (clone 6e7)

<400> SEQUENCE: 19

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Pro Ala Gly Thr
65                  70                  75                  80

Ala Met Arg Phe Leu Thr Ala Tyr Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Lys Lys Gln Thr Ile Tyr Val Glu Pro Asp

```
                    210                 215                 220
Trp Ser Ala Ala Ser Tyr Trp Tyr Ala Ile Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
                260                 265                 270

Phe Glu Ser Asp Gly Leu His Leu Asn Lys Lys Val Ile Gly Ser Asp
            275                 280                 285

Val Ser Leu Phe Asn Phe Lys Glu Cys Pro Asp Leu Ala Gln Thr Val
290                 295                 300

Val Val Val Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 20
<211> LENGTH: 416
<212> TYPE: PRT
<213> ORGANISM: Artificial Sequence
<220> FEATURE:
<223> OTHER INFORMATION: GRG31 variant (triple EK)

<400> SEQUENCE: 20

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Pro Ala Gly Thr
65                  70                  75                  80

Ala Met Arg Phe Leu Thr Ala Tyr Leu Asn Leu Val Lys Gly Ser Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175
```

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Val Ile Lys
        195                 200                 205

Ile Ala Pro Gln Ala Phe Lys Lys Gln Thr Ile Tyr Val Glu Pro Asp
210                 215                 220

Trp Ser Ala Ala Ser Tyr Trp Tyr Ala Ile Ala Leu Ala Asp Ala
225                 230                 235                 240

Asn Ala Ser Ile Val Leu Pro Gly Leu Arg Lys Asn Ser Leu Gln Gly
            245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
            275                 280                 285

Val Ser Leu Phe Asn Phe Lys Glu Cys Pro Asp Leu Ala Gln Thr Val
            290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 21
<211> LENGTH: 416
<212> TYPE: PRT
<213> ORGANISM: Artificial Sequence
<220> FEATURE:
<223> OTHER INFORMATION: GRG31 variant (L3P2c11+6e7)

<400> SEQUENCE: 21

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Pro Ala Gly Thr
65                  70                  75                  80

Ala Met Arg Phe Leu Thr Ala Phe Leu Asn Leu Val Lys Gly Asn Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

```
Val Gly Tyr Pro Pro Leu Lys Ile Glu Gly Gly Leu Phe Gln Glu Lys
            130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Lys Lys Gln Thr Ile Tyr Val Glu Pro Asp
210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 22
<211> LENGTH: 416
<212> TYPE: PRT
<213> ORGANISM: Artificial Sequence
<220> FEATURE:
<223> OTHER INFORMATION: GRG31 variant (L3P2b11+6e)

<400> SEQUENCE: 22

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Gln Ala Gly Thr
65                  70                  75                  80

Ser Leu Arg Phe Leu Thr Ala Phe Leu Asn Leu Val Lys Gly Asn Phe
```

-continued

```
                     85                  90                  95
Ile Leu Thr Gly Thr Glu Arg Met Gln Gln Arg Pro Ile Gly Ile Leu
                100                 105                 110

Val Asp Ala Met Lys Glu Ile Gly Ala Asp Ile His Tyr Asp Lys Lys
            115                 120                 125

Val Gly Tyr Pro Pro Leu Lys Ile Glu Gly Gly Leu Phe Gln Glu Lys
        130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Ala Ile Lys
        195                 200                 205

Ile Ala Pro Gln Ala Phe Lys Lys Gln Thr Ile Tyr Val Glu Pro Asp
    210                 215                 220

Trp Ser Ala Ala Ser Tyr Trp Tyr Ala Ile Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 23
<211> LENGTH: 416
<212> TYPE: PRT
<213> ORGANISM: Artificial Sequence
<220> FEATURE:
<223> OTHER INFORMATION: GRG31 variant (L3P2c11+triple EK)

<400> SEQUENCE: 23

Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45
```

-continued

```
Glu Ala Ala Asp Thr Val Thr Leu Asn Arg Val Leu Gln Ile Ala Ser
 50                  55                  60

Asp Pro Lys Pro Gly Phe Asn Thr Ile Asp Ile Gly Pro Ala Gly Thr
 65                  70                  75                  80

Ala Met Arg Phe Leu Thr Ala Phe Leu Asn Leu Val Lys Gly Ser Phe
                 85                  90                  95

Ile Leu Thr Gly Thr Glu Arg Met Gln Gln Arg Pro Ile Gly Ile Leu
                100                 105                 110

Val Asp Ala Met Lys Glu Ile Gly Ala Asp Ile His Tyr Asp Lys Lys
            115                 120                 125

Val Gly Tyr Pro Pro Leu Lys Ile Glu Gly Gly Leu Phe Gln Glu Lys
        130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Val Ile Lys
        195                 200                 205

Ile Ala Pro Gln Ala Phe Lys Lys Gln Thr Ile Tyr Val Glu Pro Asp
210                 215                 220

Trp Ser Ala Ala Ser Tyr Trp Tyr Ala Ile Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
290                 295                 300

Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 24
<211> LENGTH: 416
<212> TYPE: PRT
<213> ORGANISM: Artificial Sequence
<220> FEATURE:
<223> OTHER INFORMATION: GRG31 variant (L3P2b11+triple EK)

<400> SEQUENCE: 24
```

```
Met Asn Gln Gln Val Ile Thr Leu Thr His Pro Ser Lys Lys Ile Gln
 1               5                  10                  15
Gly Thr Val Gln Leu Thr Gly Ser Lys Ser Glu Ser Asn Arg Ala Leu
                 20                  25                  30
Ile Ile Gln Ser Leu Ser Lys Gly Gln Val Glu Ile Ala Asn Leu Ser
             35                  40                  45
Glu Ala Ala Asp Thr Val Thr Leu Asn Arg Val Leu Gln Ile Ala Ser
 50                  55                  60
Asp Pro Lys Pro Gly Phe Asn Thr Ile Asp Ile Gly Gln Ala Gly Thr
 65                  70                  75                  80
Ser Leu Arg Phe Leu Thr Ala Phe Leu Asn Leu Val Lys Gly Ser Phe
                 85                  90                  95
Ile Leu Thr Gly Thr Glu Arg Met Gln Gln Arg Pro Ile Gly Ile Leu
            100                 105                 110
Val Asp Ala Met Lys Glu Ile Gly Ala Asp Ile His Tyr Asp Lys Lys
            115                 120                 125
Val Gly Tyr Pro Pro Leu Lys Ile Glu Gly Gly Leu Phe Gln Glu Lys
130                 135                 140
Asp Arg Val Lys Ile Lys Gly Asn Ile Ser Ser Gln Tyr Ile Ser Ala
145                 150                 155                 160
Leu Leu Leu Ile Ala Pro Ala Leu Lys Lys Gly Leu Thr Leu Glu Ile
                165                 170                 175
Glu Gly Glu Leu Thr Ser Arg Pro Tyr Val Ser Met Thr Leu Asp Met
            180                 185                 190
Leu Lys Ser Val Gly Ile Gln His Glu Trp Lys Asn Asn Val Ile Lys
            195                 200                 205
Ile Ala Pro Gln Ala Phe Lys Lys Gln Thr Ile Tyr Val Glu Pro Asp
210                 215                 220
Trp Ser Ala Ala Ser Tyr Trp Tyr Ala Ile Ala Ala Leu Ala Asp Ala
225                 230                 235                 240
Asn Ala Ser Ile Val Leu Pro Gly Leu Arg Lys Asn Ser Leu Gln Gly
                245                 250                 255
Asp Ile Ala Ile Ile Ser Ile Met Glu His Phe Gly Val Gln Ser Ser
            260                 265                 270
Phe Glu Ser Asp Gly Leu His Leu Asn Lys Lys Val Ile Gly Ser Asp
            275                 280                 285
Val Ser Leu Phe Asn Phe Lys Glu Cys Pro Asp Leu Ala Gln Thr Val
290                 295                 300
Val Val Ala Ala Ala Leu Lys Arg Asp Val Ser Phe Thr Gly Leu
305                 310                 315                 320
Glu Thr Leu Lys Ile Lys Glu Thr Asp Arg Ile Ala Ala Leu Gln Lys
                325                 330                 335
Glu Ile Ala Lys Phe Gly Ala Glu Leu Ile Glu Asp Gly Asp Thr Tyr
            340                 345                 350
His Leu Lys Thr Ala Gln Val Tyr Gln Pro Glu Glu Val Thr Phe Asp
            355                 360                 365
Thr Tyr Glu Asp His Arg Met Ala Met Ala Phe Ala Pro Leu Ala Leu
370                 375                 380
Val Phe Asp Gln Ile Lys Ile Ala Glu Pro Gln Val Val Glu Lys Ser
385                 390                 395                 400
Tyr Pro Asp Phe Trp Asn His Leu Gln Ala Gln Ala Phe Val Ile Glu
                405                 410                 415
```

<210> SEQ ID NO 25

<211> LENGTH: 416
<212> TYPE: PRT
<213> ORGANISM: Artificial Sequence
<220> FEATURE:
<223> OTHER INFORMATION: GRG31 variant (L3P2c11+6b2)

<400> SEQUENCE: 25

```
Met Asn Gln Gln Val Ile Thr Leu Thr His Pro Ser Lys Lys Ile Gln
 1               5                  10                  15

Gly Thr Val Gln Leu Thr Gly Ser Lys Ser Glu Ser Asn Arg Ala Leu
             20                  25                  30

Ile Ile Gln Ser Leu Ser Lys Gly Gln Val Glu Ile Ala Asn Leu Ser
         35                  40                  45

Glu Ala Ala Asp Thr Val Thr Leu Asn Arg Val Leu Gln Ile Ala Ser
 50                  55                  60

Asp Pro Lys Pro Gly Phe Asn Thr Ile Asp Ile Gly Pro Ala Gly Thr
 65                  70                  75                  80

Ala Met Arg Phe Leu Thr Ala Phe Leu Asn Leu Val Lys Gly Ser Phe
                 85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Val Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
            340                 345                 350

His Leu Lys Thr Ala Gln Val Tyr Gln Pro Glu Glu Val Thr Phe Asp
        355                 360                 365

Thr Tyr Glu Asp His Arg Met Ala Met Ala Phe Ala Pro Leu Ala Leu
    370                 375                 380
```

```
Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
            405                 410                 415
```

<210> SEQ ID NO 26
<211> LENGTH: 416
<212> TYPE: PRT
<213> ORGANISM: Artificial Sequence
<220> FEATURE:
<223> OTHER INFORMATION: GRG31 variant (L3P2b11+6b2)

<400> SEQUENCE: 26

```
Met Asn Gln Gln Val Ile Thr Leu Thr His Pro Ser Lys Lys Ile Gln
1               5                   10                  15

Gly Thr Val Gln Leu Thr Gly Ser Lys Ser Glu Ser Asn Arg Ala Leu
            20                  25                  30

Ile Ile Gln Ser Leu Ser Lys Gly Gln Val Glu Ile Ala Asn Leu Ser
        35                  40                  45

Glu Ala Ala Asp Thr Val Thr Leu Asn Arg Val Leu Gln Ile Ala Ser
    50                  55                  60

Asp Pro Lys Pro Gly Phe Asn Thr Ile Asp Ile Gly Gln Ala Gly Thr
65                  70                  75                  80

Ser Leu Arg Phe Leu Thr Ala Phe Leu Asn Leu Val Lys Gly Ser Phe
                85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Val Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
    290                 295                 300

Val Val Val Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
```

```
                    340                 345                 350
His Leu Lys Thr Ala Gln Val Tyr Gln Pro Glu Glu Val Thr Phe Asp
            355                 360                 365

Thr Tyr Glu Asp His Arg Met Ala Met Ala Phe Ala Pro Leu Ala Leu
        370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 27
<211> LENGTH: 447
<212> TYPE: PRT
<213> ORGANISM: Artificial Sequence
<220> FEATURE:
<223> OTHER INFORMATION: GRG36 variant (GRG36(ace7))

<400> SEQUENCE: 27

Met Lys Asn Gln Asn Phe Asp Ala Lys Ala Arg Ser Pro Trp Thr Pro
1               5                   10                  15

Leu Lys Gly Val Asn Lys Ile Ser Val Ser Pro Ser Lys Gly Arg Ile
            20                  25                  30

Asn Gly Thr Val Thr Ile Pro Gly Ser Lys Ser Leu Thr Asn Arg Ala
        35                  40                  45

Leu Ile Ile Ser Ser Leu Ala Ser Gly Lys Ser Lys Val Gln Gly Ile
    50                  55                  60

Leu Lys Ser Asp Asp Ser Phe Trp Cys Leu Asp Ser Leu Lys Lys Leu
65                  70                  75                  80

Gly Val Asn Val Lys Ile Gln Gly Asp Ile Ala Phe Ile Glu Gly Asn
                85                  90                  95

Gly Gly Lys Trp Glu Ser Gly Asp Leu Tyr Ile Gly Ala Ala Gly Thr
            100                 105                 110

Ile Ala Arg Phe Leu Pro Gly Ala Leu Ala Val Ser Gly Thr Gly Ile
        115                 120                 125

Trp Glu Leu Glu Ala Ser Lys Ser Met Ser Lys Arg Pro Ile Ser Pro
    130                 135                 140

Gln Val Asp Ala Leu Lys Glu Leu Gly Ala Glu Ile Thr Tyr Leu Ser
145                 150                 155                 160

Asp Gln Gly Tyr Tyr Pro Leu Leu Val Lys Gly Lys Gln Leu Asn Gly
                165                 170                 175

Gly Glu Val Glu Leu Ser Gly Arg Ile Ser Ser Gln Phe Ile Ser Gly
            180                 185                 190

Leu Leu Ile Ala Ser Pro Tyr Leu Asn Asp Pro Ile Lys Ile Asn Ile
        195                 200                 205

Lys Asp His Ile Val Gln His Ser Tyr Val Leu Leu Thr Leu Glu Leu
    210                 215                 220

Met Lys Lys Phe Gly Ala Lys Val Lys Tyr Asp Ser Ser Leu Lys Glu
225                 230                 235                 240

Ile Val Val Tyr Pro Ser Lys Tyr Thr Pro Gln Asp Ile Asn Leu Glu
                245                 250                 255

Ala Asp Val Ser Thr Ala Cys Tyr Phe Leu Ala Leu Ala Ala Val Thr
            260                 265                 270

Asn Gly Lys Val Gln Ile Asp Asn Leu Thr Tyr Glu Thr Lys Gln Pro
        275                 280                 285

Asp Ile Lys Met Val Asp Ile Leu Glu Arg Met Gly Cys Lys Val Thr
    290                 295                 300
```

```
Arg Gly Ser Ser Phe Ile Glu Ile Glu Gly Val Ser Gln Leu Lys Gly
305                 310                 315                 320

Gly Phe Glu Ile Ser Met Arg Glu Met Ser Asp Gln Val Leu Thr Leu
            325                 330                 335

Ala Ala Ile Ala Pro Phe Ala Asp Glu Pro Ile Thr Ile Lys Asp Val
            340                 345                 350

Glu His Ile Arg His His Glu Ser Asn Arg Ile Ser Val Leu Val Asp
            355                 360                 365

Ser Leu Ser Arg Leu Gly Ile Ile Val Glu Glu Phe Lys Asp Gly Leu
    370                 375                 380

Lys Val Tyr Pro Gly Asn Pro Lys Ala Thr Leu Leu Asp Thr His Asp
385                 390                 395                 400

Asp His Arg Val Ala Met Ala Leu Ser Leu Ile Gly Ser Arg Val Glu
            405                 410                 415

Gly Ile Gln Ile Asn Asp Pro Gly Cys Val Ser Lys Thr Cys Pro Gln
            420                 425                 430

Tyr Phe Glu Leu Leu Glu Lys Leu Gly Leu Asn Ile Ile Lys His
            435                 440                 445

<210> SEQ ID NO 28
<211> LENGTH: 447
<212> TYPE: PRT
<213> ORGANISM: Artificial Sequence
<220> FEATURE:
<223> OTHER INFORMATION: GRG36 variant (GRG36(ace8))

<400> SEQUENCE: 28

Met Lys Asn Gln Asn Phe Asp Ala Lys Ala Arg Ser Pro Trp Thr Pro
1               5                   10                  15

Leu Lys Gly Val Asn Lys Ile Ser Val Ser Pro Ser Lys Gly Arg Ile
            20                  25                  30

Asn Gly Thr Val Thr Ile Pro Gly Ser Lys Ser Leu Thr Asn Arg Ala
        35                  40                  45

Leu Ile Ile Ser Ser Leu Ala Ser Gly Lys Ser Lys Val Gln Gly Ile
50                  55                  60

Leu Lys Ser Asp Asp Ser Phe Trp Cys Leu Asp Ser Leu Lys Lys Leu
65                  70                  75                  80

Gly Val Asn Val Lys Ile Gln Gly Asp Thr Ala Phe Ile Glu Gly Asn
                85                  90                  95

Gly Gly Lys Trp Glu Ser Gly Asp Leu Tyr Ile Gly Ala Ala Gly Thr
            100                 105                 110

Ile Ala Arg Phe Leu Pro Gly Ala Leu Ala Val Ser Gly Thr Gly Ile
            115                 120                 125

Trp Glu Leu Glu Ala Ser Lys Ser Met Ser Lys Arg Pro Ile Ser Pro
130                 135                 140

Leu Val Asp Ala Leu Lys Glu Leu Gly Ala Glu Ile Thr Tyr Leu Ser
145                 150                 155                 160

Asp Gln Gly Tyr Tyr Pro Leu Leu Val Lys Gly Lys Gln Leu Asn Gly
            165                 170                 175

Gly Glu Val Glu Leu Ser Gly Arg Ile Ser Ser Gln Phe Ile Ser Gly
            180                 185                 190

Leu Leu Ile Ala Ser Pro Tyr Leu Asn Asp Pro Ile Lys Ile Asn Ile
            195                 200                 205

Lys Asp His Ile Val Gln His Ser Tyr Val Leu Thr Leu Glu Leu
    210                 215                 220
```

```
Met Lys Lys Phe Gly Ala Lys Val Lys Tyr Asp Ser Ser Leu Lys Glu
225                 230                 235                 240

Ile Val Val Tyr Pro Ser Lys Tyr Thr Pro Gln Asp Ile Asn Leu Glu
            245                 250                 255

Ala Asp Val Ser Thr Ala Cys Tyr Phe Leu Ala Leu Ala Ala Val Thr
        260                 265                 270

Asn Gly Lys Val Gln Ile Asp Asn Leu Thr Tyr Glu Thr Lys Gln Pro
    275                 280                 285

Asp Ile Lys Met Val Asp Ile Leu Glu Arg Met Gly Cys Lys Val Thr
290                 295                 300

Arg Gly Ser Ser Phe Ile Glu Ile Glu Gly Val Ser Gln Leu Lys Gly
305                 310                 315                 320

Gly Phe Glu Ile Ser Met Arg Glu Met Ser Asp Gln Val Leu Thr Leu
                325                 330                 335

Ala Ala Ile Ala Pro Phe Ala Asp Glu Pro Ile Thr Ile Thr Asp Val
            340                 345                 350

Glu His Ile Arg His His Glu Ser Asn Arg Ile Ser Val Leu Val Asp
        355                 360                 365

Ser Leu Ser Arg Leu Gly Ile Ile Val Glu Glu Phe Lys Asp Gly Leu
    370                 375                 380

Lys Val Tyr Pro Gly Asn Pro Lys Ala Thr Leu Leu Asp Thr His Asp
385                 390                 395                 400

Asp His Arg Val Ala Met Ala Leu Ser Met Ile Gly Ser Arg Val Glu
                405                 410                 415

Gly Ile Gln Ile Asn Asp Pro Gly Cys Val Ser Lys Thr Cys Pro Gln
            420                 425                 430

Tyr Phe Glu Leu Leu Glu Lys Leu Gly Leu Asn Ile Ile Lys His
        435                 440                 445

<210> SEQ ID NO 29
<211> LENGTH: 1377
<212> TYPE: DNA
<213> ORGANISM: Artificial Sequence
<220> FEATURE:
<223> OTHER INFORMATION: synthetic sequence encoding GRG36 variant
      (GRG36(ace7))

<400> SEQUENCE: 29
atggcacatc accaccacca tcacggatcc ggcatgaaga accagaactt cgacgccaag        60
gcaagaagcc cctggacgcc gctcaagggc gtcaacaaga tctccgtctc gccaagcaaa       120
ggaaggatca atggcaccgt caccatccct ggaagcaaga gcttgacaaa tagagctctc       180
atcatcagca gcctagcaag cggcaagagc aaggttcaag gcatcctcaa gagcgacgac       240
agcttctggt gcctggattc attgaagaag ctcggcgtca atgtgaagat ccaaggagac       300
atcgccttca ttgaaggaaa tggaggaaaa tgggagagtg agatctctca tcggcgcc        360 gccggcacca ttgcaagatt tcttcctggc gcgctggcgg tgagcggcac aggcatctgg       420
gagctggagg caagcaagag catgagcaag aggcccatct accgcaggt ggatgctctc        480 aaggagctcg gcgccgagat cacctacctc tctgatcaag gctactaccc gctgctggtg       540
aagggcaagc agctcaatgg aggagaggtg agctctctg aaggatcag cagccagttc         600 atcagcggcc tgctgattgc ttcaccatat ttgaatgatc ccatcaagat caacatcaag       660
gaccacatcg tgcagcacag ctatgtgctg ctgacgctgg agctgatgaa gaagttcggc       720
gccaaggtga gtacgacag cagcttgaag gagatcgtcg tctacccaag caagtacacg        780
ccgcaggaca tcaacctgga agctgatgtt tcaacagcat gctacttcct ggcgctggcg       840
```

```
gcggtgacaa atggtaaggt gcaaattgac aacctcacct acgagaccaa gcagccggac    900
atcaagatgg tggacatcct ggagagaatg ggctgcaagg tgacaagagg aagcagcttc    960
atcgagattg aaggagtgag ccagctgaag ggcggcttcg agatctcaat gagggagatg   1020
agcgaccagg tgctgacgct ggcggccatc gcgccatttg ctgatgagcc catcaccatc   1080
aaggatgtgg agcacatccg ccatcatgaa agcaacagga tctccgtgct ggtggacagc   1140
ctctcaaggc tgggcatcat cgtggaggag ttcaaggatg gcctcaaggt gtaccctgga   1200
aatccaaagg cgacgctgct ggacacccat gatgatcacc gcgtggcaat ggcgctgagc   1260
ttgattggat caagggtgga aggcatccag atcaatgatc ctggctgcgt cagcaagacc   1320 tgcccctcaat attttgagct gctggagaag ctgggcctca acatcatcaa gcactag     1377
```

<210> SEQ ID NO 30
<211> LENGTH: 1377
<212> TYPE: DNA
<213> ORGANISM: Artificial Sequence
<220> FEATURE:
<223> OTHER INFORMATION: synthetic sequence encoding GRG36 variant
      (GRG36(ace8))

<400> SEQUENCE: 30

```
atggcacatc accaccacca tcacggatcc ggcatgaaga accagaactt cgacgccaag     60
gcaagaagcc cctggacgcc gctcaagggc gtcaacaaga tctccgtctc gccaagcaaa    120
ggaaggatca atggcaccgt caccatccct ggaagcaaga gcttgacaaa tagagctctc    180
atcatcagca gcttagcaag cggcaagagc aaggttcaag gcatcctcaa gagcgacgac    240
agcttctggt gcctggattc attgaagaag ctcggcgtca atgtgaagat ccaaggagac    300
accgccttca ttgaaggaaa tggaggaaaa tgggagagtg gagatctcta catcggcgcc    360
gccggcacca ttgcaagatt tcttcctggc gcgctggcgg tgagcggcac cggcatctgg    420
gagctggagg caagcaagag catgagcaag aggcccatct caccgctggt ggatgctctc    480
aaggagctcg gcgccgagat cacctacctc tctgatcaag gctactaccc gctgctggtg    540
aagggcaagc agctcaatgg aggagaggtg gagctctctg gaaggatcag cagccagttc    600
atcagcggcc tgctgattgc ttcaccatat ttgaatgatc ccatcaagat caacatcaag    660
gaccacatcg tgcagcacag ctatgtgctg ctgacgctgg agctgatgaa gaagttcggc    720
gccaaggtga agtacgacag cagcttgaag gagatcgtcg tctacccaag caagtacacg    780
ccgcaggaca tcaacctgga agctgatgtt tcaacagcat gctacttcct ggcgctggcg    840
gcggtgacaa atggcaaggt gcaaattgac aacctcacct acgagaccaa gcagccggac    900
atcaagatgg tggacatcct ggagaggatg ggctgcaagg tgacaagagg aagcagcttc    960
atcgagattg aaggagtgag ccagctgaag ggcggcttcg agatctcaat gagggagatg   1020
agcgaccagg tgctgacgct ggcggccatc gcgccatttg ctgatgagcc catcaccatc   1080
acggatgtgg agcacatccg ccatcatgaa agcaacagga tctccgtgct ggtggacagc   1140
ctctcaaggc tgggcatcat cgtggaggag ttcaaggacg gcctcaaggt gtaccctgga   1200
aatccaaagg cgacgctgct ggacacccat gatgatcacc gcgtggcaat ggcgctgagc   1260
atgattggat caagggtgga aggcatccag atcaatgatc ctggctgcgt cagcaagacc   1320 tgcccctcaat attttgagct gctggagaag ctgggcctca acatcatcaa gcactag     1377
```